(12) United States Patent
Sharma et al.

(10) Patent No.: US 8,581,584 B2
(45) Date of Patent: Nov. 12, 2013

(54) MEMBRANE PROTEINS, MECHANISMS OF ACTION AND USES THEREOF

(75) Inventors: Mukesh Sharma, Tallahassee, FL (US); Myunggi Yi, Busan (KR); Hao Dong, Tallahassee, FL (US); Huajun Qin, Tallahassee, FL (US); David D. Busath, Orem, UT (US); Huan-Xiang Zhou, Tallahassee, FL (US); Timothy A. Cross, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 426 days.

(21) Appl. No.: 13/067,351

(22) Filed: May 26, 2011

(65) Prior Publication Data

US 2011/0291652 A1    Dec. 1, 2011

Related U.S. Application Data

(60) Provisional application No. 61/348,437, filed on May 26, 2010.

(51) Int. Cl.
*G01V 3/00* (2006.01)

(52) U.S. Cl.
USPC .......................................... 324/309; 324/300

(58) Field of Classification Search
USPC ........................... 324/300–322; 600/407–445
See application file for complete search history.

(56) References Cited

U.S. PATENT DOCUMENTS

| | | | |
|---|---|---|---|
| 6,002,256 A * | 12/1999 | Slade | 324/322 |
| 7,970,455 B2 * | 6/2011 | Zilberstein et al. | 600/436 |
| 8,036,731 B2 * | 10/2011 | Kimchy et al. | 600/436 |
| 8,055,329 B2 * | 11/2011 | Kimchy et al. | 600/436 |
| 8,101,732 B2 * | 1/2012 | Mahmud et al. | 536/17.9 |
| 8,116,845 B2 * | 2/2012 | Hashimshony et al. | 600/421 |
| 8,476,287 B2 * | 7/2013 | Okano et al. | 514/274 |
| 2008/0287750 A1 * | 11/2008 | Hashimshony et al. | 600/301 |
| 2012/0123244 A1 * | 5/2012 | Hashimshony et al. | 600/415 |

OTHER PUBLICATIONS

J. R. Schnell, J. J. Chou, Nature 451, 591 (2008).
Sharma et al. Science, Oct. 22; 330 (6003):509-12 (2010).
M. Takeda, A. Pekosz, K. Shuck, L. H. Pinto, R. A. Lamb, J. Virol. 76, 1391 (2002).
K. Nishimura, S. Kim, L. Zhang, T. A. Cross, Biochemistry 41, 13170 (2002)
J. Hu et al., Biophys. J. 92, 4335 (2007).
A. L. Stouffer et al., Nature 451, 596 (2008).
S. D. Cady, M. Hong, Proc. Natl. Acad. Sci. U. S.A. 105, 1483.
S. D. Cady et al., Nature 463, 689 (2010).

(Continued)

*Primary Examiner* — Brij Shrivastav
(74) *Attorney, Agent, or Firm* — Alchemy-Partners, PC

(57) ABSTRACT

The invention relates to the atomistic functional understanding of the M2 protein from the influenza A virus. This acid-activated selective proton channel has been the subject of numerous conductance, structural, and computational studies. Previously, little was known at the atomic level about the heart of the functional mechanism of this tetrameric protein, a tetrad of HxxxW residues. The structure of the M2 conductance domain in a lipid bilayer is disclosed and displays the defining features of the native protein that have not been attainable from structures solubilized by detergents. A detailed mechanism for acid activation and proton conductance, involving a strong hydrogen bond between two adjacent histidines and specific interactions with the tryptophan gate, is provided and elucidates many observations on the M2 proton conductance.

8 Claims, 18 Drawing Sheets

(56) References Cited

OTHER PUBLICATIONS

R. Acharya et at., Proc. Natl. Acad. Sci. U.S.A. 107, 15075 (2010).
C. Ma et al., Proc. Natl. Acad. Sci. U.S.A. 106, 12283 (2009).
J. A. Mould et al., J. Biol. Chem. 275, 8592 (2000).
C. Tian, P. F. Gao, L. H. Pinto, R. A. Lamb, T. A. Cross, Protein Sci. 12, 2597 (2003).
Y. Tang, F. Zaitseva, R. A. Lamb, L. H. Pinto, J. Biol. Chem. 277, 39880 (2002).
M. Yi, T. A. Cross, H. X. Zhou, J. Phys. Chem. B 112, 7977 (2008).
T. A. Cross, M. Sharma, M. Yi, H. X. Zhou, Trends Biochem. Sci. 36(2) 117-125 (2010).
C. Li, H. Qin, F. P. Gao, T. A. Cross, Biochim. Biophys. Acta 1768, 3162 (2007).
T. L. Lau, V. Dua, T. S. Ulmer, J. Biol. Chem. 283, 16162 (2008).
P. Venkataraman, R. A. Lamb, L. H. Pinto, J. Biol. Chem. 280, 21463 (2005).
J. Hu et al., Proc. Natl. Acad. Sci. U. S.A. 103, 6865-6870 (2006).
X. -j. Song, A. E. McDermott, Magn. Reson. Chem. 39, 537 (2001).
A. Quick, D. J. Williams, Can. J. Chem. 54, 2465 (1976).
W. Tatara, M. J. Wojcik, J. Lindgren, M. Probst, J. Phys. Chem. A 107, 7827 (2003).
A. Okada, T. Miura, H. Takeuchi, Biochemistry 40, 6053 (2001).
L.H. Pinto et al., Proc. Natl. Acad. Sci. U.S.A. 94, 11301-11306 (1997).
M. Yi, T. A. Cross, H, X. Zhou, Proc. Natl. Acad. Sci. U.S.A. 106, 13311-13316 (2009).
I.V. Chizhmakov et al., J. Physiol. 494, 329-336 (1996).
I.V. Chizhmakov et al., J. Physiol. 546, 427-438 (2003).
T. I. Lin, C. Schroeder, J. Virol. 75, 3647-3656 (2001).
Andre et al., "Increased immune response elicited by DNA vaccination with a synthetic gp120 Sequence with Optimized Codon Usage," J. Virol. 72:1497-1503 (1998).
Karlin et al., "Methods for assessing the statistical significance of molecular sequence features by using general scoring schemes," Proc. Natl. Acad. Sci. 87: 2264-2268 (1990).
Karlin et al., "Applications and statistics for multiple high-scoring segments in molecular sequences," Proc. Natl. Acad. Sci. 90: 5873-5877 (1993).
Myers et al., "Optimal alignments in linear space," CABIOS 4: 11-17 (1988).
Pearson et al., "Improved tools for biological sequence comparison," Proc. Natl. Acad. Sci. 85: 2444-2448 (1988).
Altschul et al., "Local Alignment Statistics," Methods in Enzymology, Doolittle ed., 266: 460-480 (1996).
Altschul et al., "Basic Local Alignment Search Tool," J. Mol. Biol., 215: 403-410 (1990).
Gish et al., "Identification of Protein Coding Regions by Database Similarity Search," Nature Genetics 3: 266-272 (1993).
J. Hu et al.,"Structural Biology of Transmembrane Domains: Efficient Production and Characterization of Transmembrane Peptides by NMR," Protein Sci. 16, 2153-2165 (2007).
P. L. Gor'kov et al., "Using Low-E Resonators to Reduce RF Heating in Biological Samples for Static Solid-State NMR up to 900 MHz," J. Magn. Reson. 185, 77-93 (2007).
A. Ramamoorthy, S. J. Opella, Solid State Nucl. Magn. Reson. 4, 387-392 (1995).
A. A. Nevzorov, S. J. Opella, J. Magn. Reson. 164, 182-186(2003).
F. M. Marassi, S. J. Opella, J. Magn. Reson. 144, 150-155 (2000).
J. Wang et al., J. Magn. Reson. 144, 162-167 (2000).
N.J. Traaseth et al, Proc. NatL Acad. Sci. USA 104, 14676-14681 (2007).
R. Fu, E. D. Gordon, D. J. Hibbard, M. Cotten, J. Am. Chem. Soc. 131, 10830-10831 (2009).
T. Asbury et al, J. Magn. Reson. 183, 87-95 (2006).
C.D. Schwieters, J. J. Kuszewski, N. Tjandra, G. M. Clore, J. Magn. Reson. 160, 65-73 (2003).
M. Nilges, A Calculation Strategy for the Structure Determination of Symmetric Dimers by $^1$H NMR, Proteins 17, 297-309(1993).
S.I. O'Donoghue, G. F. King, M. Nilges, J. Biomol. NMR 8, 193-206 (1996).
P.A. Nguyen et al, Biochemistry 47, 9934-9936 (2008).
S. Jo, T. Kim, W. Im, PLoS One 2, e880 (2007).
J.C. Phillips et al., J Comput Chem 26, 1781-1802 (2005).
N. Kucerka et al., Biophys J 95, 2356-2367 (2008).
A. D. MacKerell et al., Journal of Physical Chemistry B 102, 3586-3616 (1998).
A. D. Mackerell, M. Feig, C. L. Brooks, Journal of Computational Chemistry 25, 1400-1415 (2004).
Toukmaji, C. Sagui, J. Board, T. Darden, Journal of Chemical Physics 113, 10913 (2000).
T. Schlick et al., Journal of Computational Physics 151, 9-48 (1999).
G. J. Martyna, D. J. Tobias, M. L. Klein, Journal of Chemical Physics 101, 4177 (1994).
S. E. Feller, Y. H. Zhang, R. W. Pastor, B. R. Brooks, Journal of Chemical Physics 103, 4613 (1995).
S. Dapprich, I. Komaromi, K. S. Byun, K. Morokuma, M. J. Frisch, Journal of Molecular Structure-Theochem 462, 1-21 (1999).
R. Witter et al., Proc. WSEAS: Biochem. Med. Chem., in press (2010).
J.C. Moffat et al., Biophys J vol. 94, 434-445 (2008).
O. S. Smart, J. G. Neduvelil, X. Wang, B. A. Wallace, M. S. Sansom, J. Mol. Graph. 14, 354-360 (1996).
R. M. Pielak, J. R. Schnell, J. J. Chou, Proc. Natl. Acad. Sci. USA 106, 7379-7384 (2009).
G. G. Kochendoerfer et al., Biochemistry 38, 11905-11913 (1999).

* cited by examiner

US 8,581,584 B2

MEMBRANE PROTEINS, MECHANISMS OF ACTION AND USES THEREOF

CROSS-REFERENCE TO RELATED APPLICATIONS

This application claims benefit of priority to U.S. Provisional Patent Application No. 61/348,437 entitled a "Atomistic Mechanism of Influenza A M2 Protein from Structure determined in Lipid Bilayer" filed May 26, 2010, the entire contents and disclosure of which is incorporated herein by reference.

GOVERNMENT INTEREST STATEMENT

The United States Government has rights in this invention pursuant to funding obtained from the National Institute of Allergy and Infectious Diseases grant AI023007. The spectroscopy was conducted at the National High Magnetic Field Laboratory supported by Cooperative Agreement 0654118 between the NSF Division of Materials Research and the State of Florida.

BACKGROUND

1. Field of the Invention
The present invention relates generally to viral proteins.
2. Related Art
The M2 protein from the influenza A virus, an acid-activated proton-selective channel, has been the subject of numerous conductance, structural, and computational studies. However, little is known at the atomic level about the heart of the functional mechanism for this tetrameric protein, a $His^{37}$-$Trp^{41}$ cluster. The structure of a similar construct of this protein solubilized in detergent micelles as further described in J. R. Schnell, J. J. Chou, Nature 451, 591 (2008), failed to explain the main observations on M2 proton conductance and also generated artifacts that were likely to be a result of the detergent environment used for that structural characterization.

SUMMARY

According to one broad aspect, the present invention provides a method comprising the following steps: (a) providing a first solid-state NMR spectrum and a second solid-state NMR spectrum, and (b) detecting a change in resonance of a labeled isotope based on comparing the second solid-state NMR spectrum to the first solid-state NMR spectrum to thereby determine that a drug candidate has bound to a histidine tetrad of a viral protein, wherein second solid-state NMR spectrum is for a first uniformly aligned sample of the viral protein, and wherein the second solid-state spectrum is for a second uniformly aligned sample of the viral protein after being treated with the drug candidate.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Terminology

Figure 1:
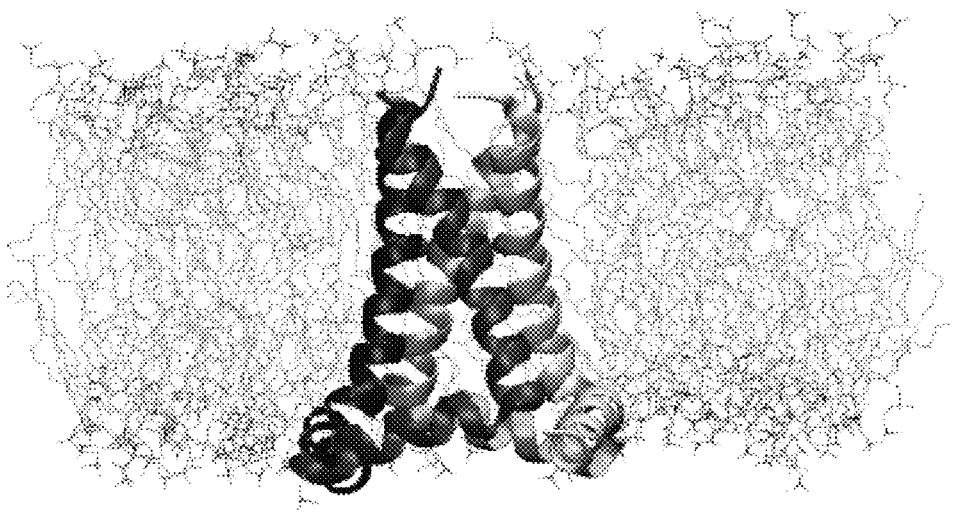
FIG. 1 is a schematic illustration showing the tetrameric structure of the M2 conductance domain, solved by solid-state NMR spectroscopy and restrained molecular dynamics simulations, in liquid crystalline lipid bilayers.

Where the meaning of terms departs from the commonly used meaning of the term, applicant intends to utilize the terminology provided below, unless specifically indicated.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "bind," the term "binding" and the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "biological sample" and the term "biological specimen" refers to either a part or the whole of a human, animal, microbe or plant in vitro or in vivo. The term includes but is not limited to material of human, animal, microbe or plant origin such as human, animal, microbial or plant tissue sections, cell or tissue cultures, suspension of human, animal, microbial or plant cells or isolated parts thereof, human or animal biopsies, blood samples, cell-containing fluids and secretion.

For purposes of the present invention, the term "channel protein" or "ion-channel protein" refers to pore-forming proteins that help establish and control the small voltage gradient across the plasma membrane of cells by allowing the flow of ions down their electrochemical gradient. They are present in the membranes that surround all biological cells. A "proton channel protein" refers to a proton-selective ion channel protein.

For purposes of the present invention, the term "drug candidate" refers to a naturally occurring or synthetic compound or a combination thereof that is identified to act on a particular target. A target generally refers to a naturally existing cellular or molecular structure involved in the pathology of interest. A good drug candidate exhibits features like increased activity against a chosen target, reduced activity against unrelated targets and improved druglikeness properties. Drug candidates include but are not limited to natural products, plant-derived extracts, microbial metabolites, agents from marine invertebrates, compounds generated through combinatorial chemistry, synthetic or man-made compounds, semi-synthetic derivatives of natural products or small molecules.

For purposes of the present invention, the term "drug" means any compound intended for use in the diagnosis, cure, mitigation, treatment, or prevention of disease in a human subject or other animals.

For purposes of the present invention, the term "epitope" refers to the smallest part of an antigen moiety recognizable by the combining site of an immunoglobulin.

For purposes of the present invention, the term "exogenous material" refers to material that originates outside the organism of concern or material that may be isolated from a organism, manipulated to any extent externally and then reintroduced into its natural environment or the environment from which it was isolated. Exogenous material includes but is not limited to nucleic acids, proteins, polymeric compounds, particulate matter and artificially synthesized material. For example, "exogenous nucleic acid" refers to any nucleic acid, DNA or RNA or fragments thereof, either single or double stranded, that originates outside of the organism of concern or was isolated from the organism, modified and reintroduced into the organism. Exogenous DNA present in a host cell may be derived from a source organism, cloned into a vector and then introduced into a host cell.

For purposes of the present invention, the term "immune response" refers to a specific response of the immune system of an animal to antigen or immunogen. Immune response may include the production of antibodies and cellular immunity.

For purposes of the present invention, the term "immunity" refers to a state of resistance of a subject animal including a human to an infecting organism or substance. It will be understood that an infecting organism or substance is defined broadly and includes parasites, toxic substances, cancer cells and other cells as well as bacteria and viruses. A "Therapeutically Effective Immunization Course" (see below for definition) will produce the immune response.

For purposes of the present invention, the term "immunization conditions" refers to factors that affect an immune response including the amount and kind of immunogen or adjuvant delivered to a subject animal including a human, method of delivery, number of inoculations, interval of inoculations, the type of subject animal and its condition. "Vaccine" refers to pharmaceutical formulations able to induce immunity.

For purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant but will generally be between about 0.1 μg/ml or less and about 100 μg per inoculation. The immunization dose is easily determined by methods well known to those skilled in the art, such as by conducting statistically valid host animal immunization and challenge studies as described: for example, Manual of Clinical Immunology, H. R. Rose and H. Friedman, American Society for Microbiology, Washington, D.C. (1980), tithe entire contents and disclosures of which are incorporated herein by reference. In some instances, several immunization doses including booster doses may administered to provide immunity, and, For purposes of the present invention such a course of treatment is collectively referred to as "Therapeutically Effective Immunization Course".

For purposes of the present invention, the term "immunogen" and the term "immunogenic" refers to a substance or material (including antigens) that is able to induce an immune response alone or in conjunction with an adjuvant. Both natural and synthetic substances may be immunogens. An immunogen is generally a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" or a composition that is "immunogenic" includes substances (e.g., small peptides) that do not generate an immune response (or generate only a therapeutically ineffective immune response) unless associated with an adjuvant. For purposes of the present invention, such immunogens are referred to as "adjuvant-obligatory" immunogens.

For purposes of the present invention, the term "immunogenic amount" is an amount of an antigen preparation of interest or amount of a biological toxin that elicits a clinically detectable protective response in an animal.

For purposes of the present invention, the term "isotope" refers to variants of atoms of a particular chemical element, which have differing numbers of neutrons. A number of isotopes may be used in NMR studies which include but are not limited to $^1H$, $^2H$, $^3He$, $^6Li$, $^7Li$, $^9Be$, $^{11}B$, $^{10}B$, $^{13}C$, $^{14}N$, $^{15}N$, $^{17}O$, $^{19}F$, $^{21}Ne$, $^{23}Na$, $^{25}Mg$, $^{27}Al$, $^{29}Si$, $^{31}P$, $^{33}S$, $^{35}Cl$, $^{37}Cl$ etc.

For purposes of the present invention, the term "label" or "marker" is a modification of a compound (e.g., a ligand or receptor) that enables the user to specifically detect the labeled compound in the presence of unlabeled compounds. For example, one or more atoms within the compound may be labeled with radioactive isotopes. Alternatively, labels may provide antigenic determinants, nucleic acids available for hybridization, altered fluorescence-polarization or altered light-scattering. Still other markers include those that are chromogenic, fluorescent, chemiluminescent or electrochemically detectable. Other methods available to label a ligand or receptor will be readily apparent to those skilled in the art.

For purposes of the present invention, the term "non-naturally occurring" or "isolated" refers to the component of interest being at least substantially free from at least one other component with which it is naturally associated in nature and as found in nature.

For purposes of the present invention, the term "peptide-like" refers to short chain peptides as well as proteins, lipoproteins and glycoproteins, but will also, for convenience, include non-proteinaceous molecules, for example, amino acid-containing molecules. In certain embodiments, the peptide-like therapeutic agent may additionally comprise vitamins, steroids, azidothymidine, and free primaquine in addition to other agents. One useful class of peptides is immunomodulators such as interleukins, colony stimulating factors and interferons. Another useful class of proteins is antigens and immunogens such as are used in vaccines.

For purposes of the present invention, the term "purified" refers to the component in a relatively pure state—e.g. at least about 90% pure, or at least about 95% pure or at least about 98% pure.

For purposes of the present invention, the term "small molecule" refers to a low molecular weight organic compound which is by definition not a polymer. The term small molecule, especially within the field of pharmacology, is usually restricted to a molecule that also binds with high affinity to a biopolymer such as protein, nucleic acid, or polysaccharide and in addition alters the activity or function of the biopolymer. The upper molecular weight limit for a small molecule may be approximately 800 Daltons which allows for the possibility to rapidly diffuse across cell membranes so that they can reach intracellular sites of action. Small molecules can have a variety of biological functions, serving as cell signaling molecules, as tools in molecular biology, as drugs in medicine, as pesticides in farming, and in many other roles. Small molecules may include but are not limited to compounds that are natural (such as secondary metabolites), artificial (such as antiviral drugs), constituent monomers of biopolymers such as ribo- or deoxyribonucleotides, amino acids, and monosaccharides, very small oligomers such as dinucleotides, peptides such as the antioxidant glutathione, and disaccharides such as sucrose.

For purposes of the present invention, the term "Solid-state NMR" refers to solid state NMR spectroscopy which is a kind of nuclear magnetic resonance (NMR) spectroscopy, characterized by the presence of anisotropic (directionally dependent) interactions. One of skill in the art is aware of the theory and applicability of NMR spectroscopy. Recent innovation within NMR spectroscopy has been within the field of protein NMR, which has become a very important technique in structural biology. A goal of these investigations is to obtain high resolution 3-dimensional structures of the protein, similar to what can be achieved by X-ray crystallography. In contrast to X-ray crystallography, NMR is used primarily on relatively small proteins though technical advances allow ever larger structures to be solved. NMR spectroscopy is advantageous to obtain high resolution information on partially or wholly intrinsically unstructured proteins. It is now a common tool for the determination of Conformation Activity Relationships where the structure before and after interaction with, for example, a drug candidate is compared to its known biochemical activity. Because of the much higher number of atoms present in a protein molecule in comparison with a small organic compound, the basic 1D spectra become crowded with overlapping signals to an extent where direct spectra analysis becomes unreasonable. Therefore, multidimensional (2, 3 or 4D) experiments have been devised to deal with this problem. To facilitate these experiments, it is desirable to isotopically label the protein with $^{13}C$ and $^{15}N$ because the predominant naturally occurring isotope $^{12}C$ is not NMR-active, whereas the nuclear quadrupole moment of the predominant naturally occurring $^{14}N$ isotope prevents high resolution information to be obtained from this nitrogen isotope. Aspects of solid state NMR are further described in U.S. Pat. Nos. 7,754,438 and 7,678,546, the contents and disclosure of which is hereby incorporated by reference in its entirety.

For purposes of the present invention, the term "uniformly aligned sample" means a sample in which each molecule in the sample will have the same orientation with respect to the magnetic field axis of the NMR spectrometer. In this way the orientation dependent spin interactions such as anisotropic chemical shifts, dipolar and quadrupolar interactions can be observed. The orientations of the individual atomic sites in the protein reflect the orientation of that particular site with respect to the magnetic field. For membrane proteins the plane of the bilayer and hence the orientation of the membrane protein spanning the membrane can be oriented with the bilayer normal either parallel or perpendicular to the magnetic field.

For purposes of the present invention, the term "viral protein" refers to proteins for viruses which include but are not limited to the following virus families: Retroviridae (for example, human immunodeficiency virus (HIV), human T-cell leukemia viruses; Picornaviridae (for example, polio virus, hepatitis A virus, hepatitis C virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus), rubella viruses); Flaviridae (for example, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, influenza viruses, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxyiridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus).

For purposes of the present invention, the terms "HxxxW quartet", HxxxW tetrad, "the histidine tetrad" and "His$^{37}$-Trp$^{41}$ cluster" are all used interchangeably and refer to the novel histidine chemistry that was identified in the M2 protein of Influenza A as described in this disclosure and in Sharma et al. *Science, October* 22; 330 (6003):509-12 (2010). These terms also encompass chemistries in proteins that include but are not limited to viral proteins that are substantially similar to the histidine tetrad in terms of sequence and function.

For purposes of the present invention, the terms "protein," "peptide," "polypeptide," and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

DESCRIPTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein and references cited within them are incorporated herein by reference in their entireties including U.S. Provisional Patent Application No. 61/348,437 entitled a "Atomistic Mechanism of Influenza A M2 Protein from Structure determined in Lipid Bilayer" filed May 26, 2010.

Influenza A and B viruses cause a highly contagious respiratory disease in humans resulting in approximately 36,000 deaths in the United States annually (Wright, P. F., and Webster, R. G. 2001. Orthomyxoviruses. 1533-79 In: *Fields Virology*, eds. D. M. Knipe and P. M. Howley, Lippincott Williams & Wilkins, Philadelphia and Prevention. 2005. Background on Influenza on the website of the Center for Disease Control and Prevention).

The M2 protein has a critical role to play in the life cycle of the influenza A virus. It is located in the viral envelope. It allows hydrogen ions to enter the viral particle (virion) from the endosome, thus lowering the pH inside of the virus, which causes dissociation of the viral matrix protein M1 from the ribonucleoprotein RNP. This is a crucial step in uncoating of the virus and exposing its content to the cytoplasm of the host cell. Hence Proton conductance by the M2 protein (with 97 residues per monomer) in influenza A is essential for viral replication as described in M. Takeda, A. Pekosz, K. Shuck, L. H. Pinto, R. A. Lamb, *J. Virol.* 76, 1391 (2002).

Antiviral drugs amantadine and rimantadine can inhibit the function of the M2 channel and blocks the virus from taking over the host cell. The drug molecule binds to the transmembrane region and sterically blocks the channel. This stops the protons from entering the virion, which subsequently does not disintegrate. However, the M2 gene is susceptible to mutations. A M2 mutation, Ser$^{31}$→Asn, in recent flu seasons and in the recent H1N1 swine flu pandemic renders the viruses resistant to amantadine and rimantadine as described in L. Gubareva et al.; Centers for Disease Control and Prevention (CDC), *Morb. Mortal. Wkly. Rep.* 58, 1 (2009). As the mutations are relatively frequent this may lead to emergence of resistant strains.

An important aspect of understanding protein function is obtaining accurate structural information at an atomic level. Structural information was previously obtained on the M2 protein when a construct (residues 18-60) was solubilized in detergent micelles as described in J. R. Schnell, J. J. Chou, *Nature* 451, 591 (2008). However the information obtained failed to explain all the main observations on M2 proton conductance and there were artifacts in the structure that were likely to be resultant of the detergent environment used for the characterization.

Previous structural determinations of M2 focused primarily on its transmembrane (TM) domain, residues 26 to 46 as further described in K. Nishimura, S. Kim, L. Zhang, T. A. Cross, *Biochemistry* 41, 13170 (2002); J. Hu et al., *Biophys. J.* 92, 4335 (2007); A. L. Stouffer et al., *Nature* 451, 596 (2008); S. D. Cady, M. Hong, *Proc. Natl. Acad. Sci.* U.S.A. 105, 1483; S. D. Cady et al., *Nature* 463, 689 (2010) and R. Acharya et at., *Proc. Natl. Acad. Sci.* U.S.A. 107, 15075 (2010).

Figure 22:
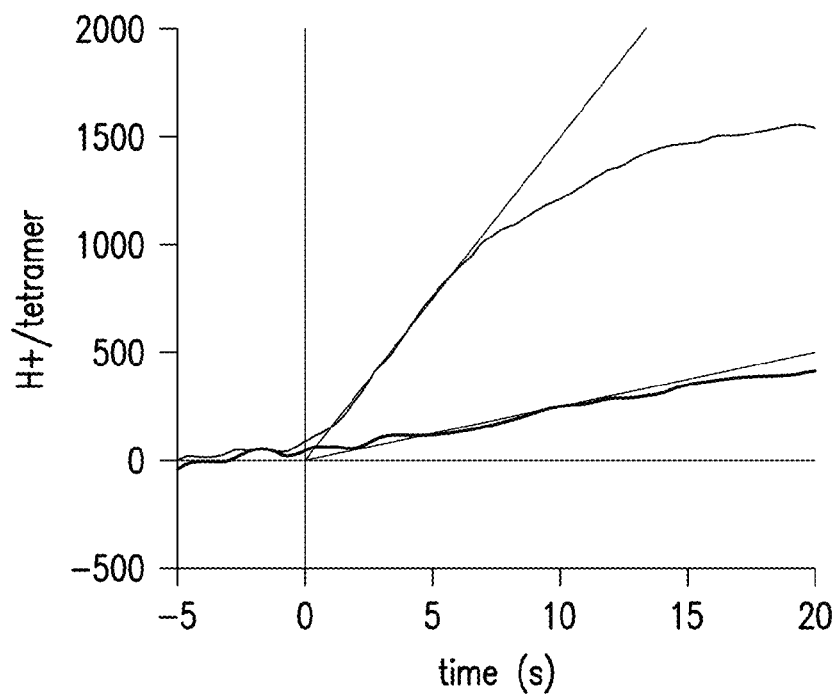
FIG. 22 is a graph showing the proton uptake per tetramer as a function of time, in the absence (blue) and presence (green) of 100 μM amantadine. pH,=5.5.
Figure 23:
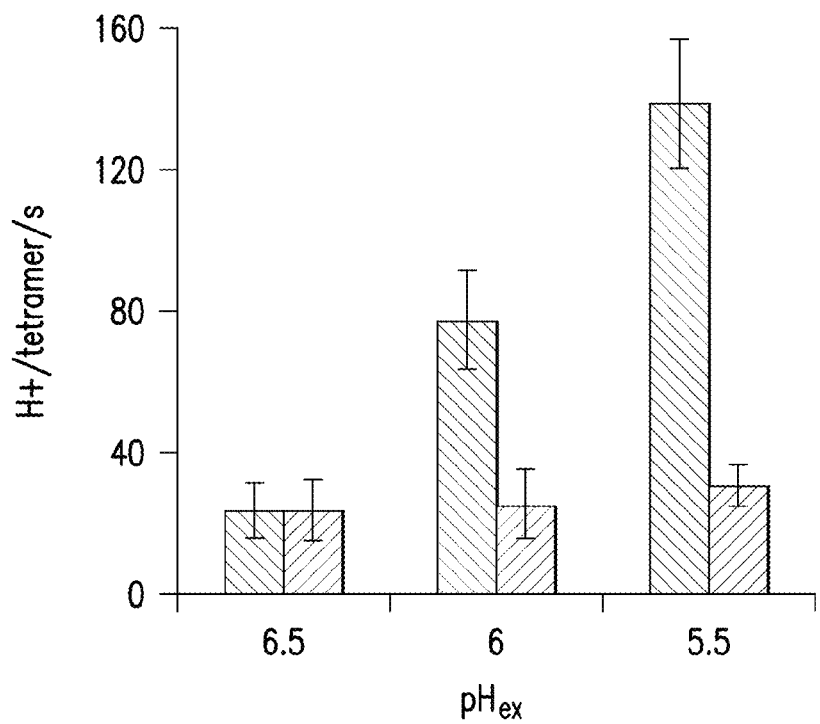
FIG. 23 is a graph showing the pH dependence of proton flux (calculated from the initial slopes illustrated in FIG. 22, without (blue) and with (green) 100 μM amantadine.

Although the TM domain is capable of conducting protons, residues 47 to 62 following the TM domain are essential for the functional integrity of the channel. Oocyte assays showed that truncations of the post-TM sequence result in reduced conductance as referred to in C. Ma et al., *Proc. Natl. Acad. Sci.* U.S.A. 106, 12283 (2009). An embodiment of the invention is the structure of the "conductance" domain, consisting of residues 22 to 62, which in liposomes conducts protons at a rate comparable to that of the full-length protein in cell membranes as described in J. A. Mould et al., *J. Biol. Chem.* 275, 8592 (2000) and T. I. Lin, C. Schroeder, *J. Virol.* 75, 3647 (2001), is amantadine-sensitive (as indicated in FIGS. 22 and 23). This structure, solved in uniformly aligned 1,2-dioleoyl-sn-glycero-3-phosphatidylcholine: 1,2-dioleoyl-sn-glycero-3-phosphoethanolamine bilayers by solid-state nuclear magnetic resonance (NMR) at pH 7.5 and 30° C., shows striking differences from the structure of a similar construct (residues 18 to 60) solubilized in detergent micelles as described in J. R. Schnell, J. J. Chou, *Nature* 451, 591 (2008).

In one embodiment, the present invention provides the structure of the M2 conductance domain (residues 22 to 62) in a lipid bilayer, which displays the defining features of the native protein that have not been attainable from structures solubilized by detergents.

In another embodiment, the present invention provides a mechanism by which the tetrameric $His^{37}$-$Trp^{41}$ cluster guides protons through the channel by forming and breaking hydrogen bonds between adjacent pairs of histidines and through specific interactions of the histidines with the tryptophan gate.

In one embodiment the present invention relates to atomic structural information of viral proteins and the use of such information to identify and design compounds, such as, but not limited to peptides, antigens, antibodies, small molecule inhibitors or activators and synthetic compounds that when administered affect viral function and may be used in diagnostic, pharmaceutical, immunogenic and immunological compositions.

Figure 2:
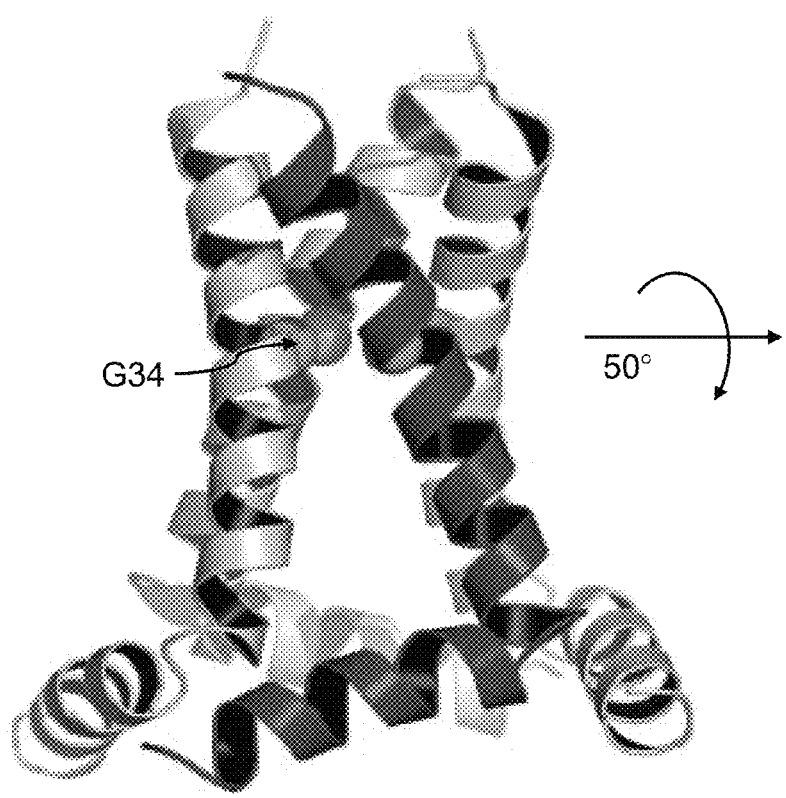
FIG. 2 is a schematic illustration showing the tetrameric structure of the M2 conductance domain, solved by solid-state NMR spectroscopy and restrained molecular dynamics simulations, in liquid crystalline lipid bilayers, wherein the structure is shown alone.
Figure 4:
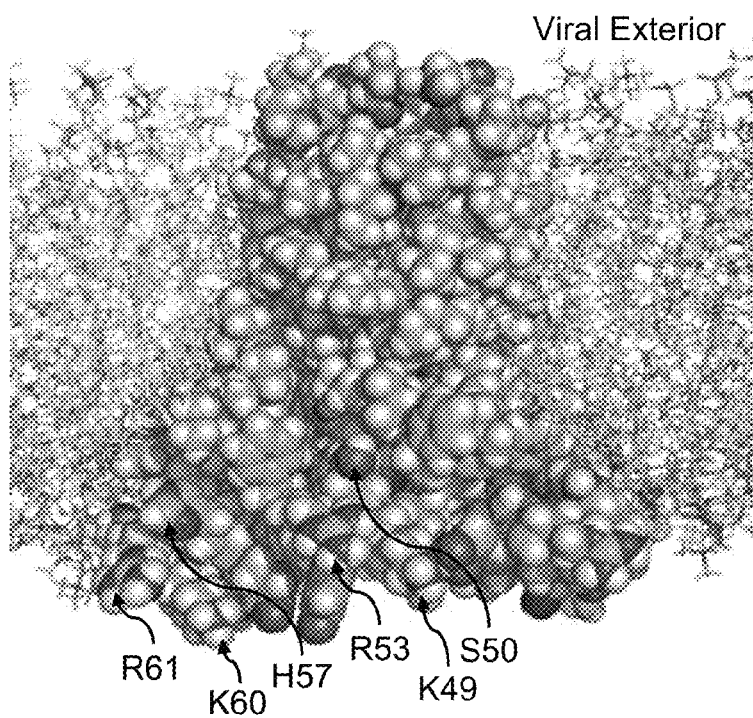
FIG. 4 is a space-filling representation of the protein side chains in the lipid bilayer environment used for the NMR spectroscopy, structural refinement, and functional assay.
Figure 24:
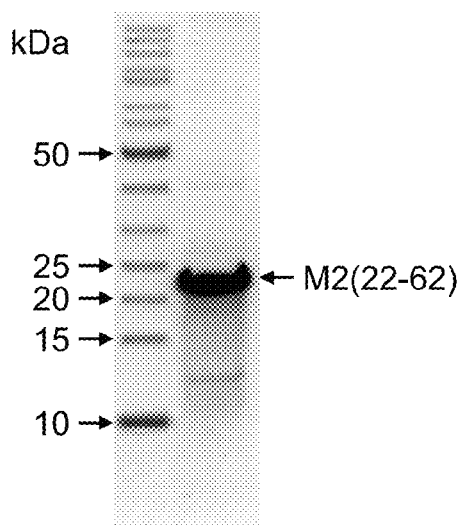
FIG. 24 is an image of an SDS-PAGE gel of the M2 conductance domain demonstrating the tetrameric state. Molecular weight markers on the left; purified protein in DDM micelles on the right.

The structure is a tetramer as seen in the SDS-PAGE gel in FIG. 24, with each monomer comprising two helices (FIG. 2). Residues 26 to 46 form a kinked TM helix, with the N-terminal and C-terminal halves having tilt angles of −32° and −22° from the bilayer normal, respectively. The kink in the TM helix occurs around $Gly^{34}$, similar to the kinked TM-domain structure in the presence of amantadine as referred to in J. Hu et al., *Biophys. J.* 92, 4335 (2007). The amphipathic helix (residues 48 to 58) has a tilt angle of 105°, similar to that observed for the full-length protein as suggested in C. Tian, P. F. Gao, L. H. Pinto, R. A. Lamb, T. A. Cross, *Protein Sci.* 12, 2597 (2003), and resides in the lipid interfacial region (FIG. 4). The turn between the TM and amphipathic helices is tight and rigid, as indicated by substantial anisotropic spin interactions for $Leu^{46}$ and $Phe^{47}$ (their resonances lie close to the TM and amphipathic helical resonance patterns, respectively; see FIGS. 25-30). The result is a structural base formed by the four amphipathic helices that stabilizes the tetramer.

Figure 6:
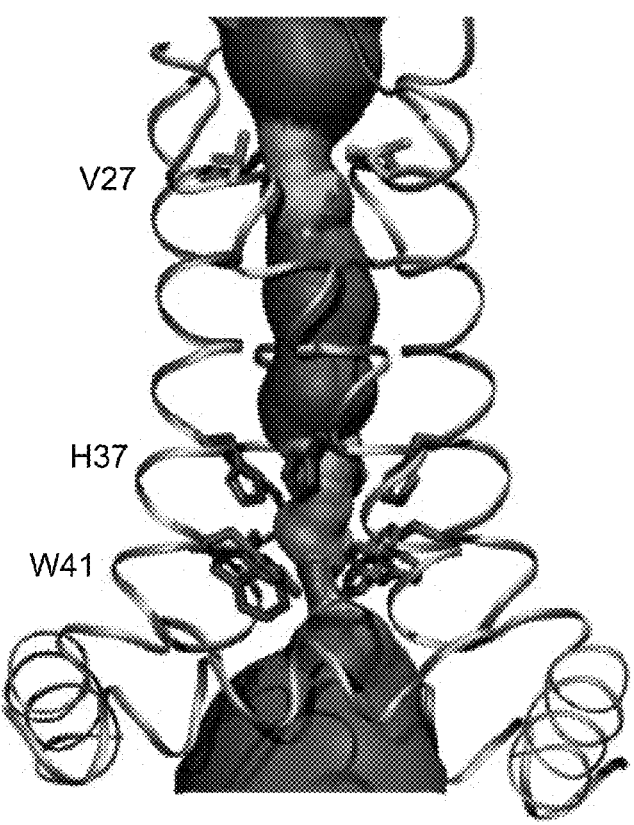
FIG. 6 is a HOLE image shows constrictions at the $Val^{27}$ secondary gate and at the unique conductance HxxxW motif, responsible for both acid activation and proton transport. The pore constriction at $Val^{21}$ and $Trp^{41}$ is illustrated.

The pore formed by the TM-helix bundle is lined by $Val^{27}$, $Ser^{31}$, $Gly^{34}$, $His^{37}$, $Trp^{41}$, $Asp^{44}$, and $Arg^{45}$, which include all of the polar residues of the TM sequence. The pore is sealed by the TM helices (FIG. 4) and constricted by $Val^{27}$ at the N-terminal entrance and by $Trp^{41}$ at the C-terminal exit (FIG. 6). The gating role of $Trp^{41}$ has long been recognized as described in Y. Tang, F. Zaitseva, R. A. Lamb, L. H. Pinto, *J. Biol. Chem.* 277, 39880 (2002), and recently $Val^{27}$ was proposed to form a secondary gate as suggested in M. Yi, T. A. Cross, H. X. Zhou, *J. Phys. Chem. B* 112, 7977 (2008). An important cavity between $Val^{27}$ and $His^{37}$ presents an amantadine-binding site as described in K. Nishimura, S. Kim, L. Zhang, T. A. Cross, *Biochemistry* 41, 13170 (2002); S. D. Cady et al., *Nature* 463, 689 (2010) and M. Yi, T. A. Cross, H. X. Zhou, *J. Phys. Chem. B* 112, 7977 (2008). This drug-binding site is eliminated in a structure solubilized in detergent micelles as described in J. R. Schnell, J. J. Chou, *Nature* 451, 591 (2008), because of a much smaller tilt angle of the TM helices as referred to in T. A. Cross, M. Sharma, M. Yi, H. X. Zhou, *Trends Biochem. Sci.* 10.1016/j.tibs.2010.07.005 (2010).

Figure 7:
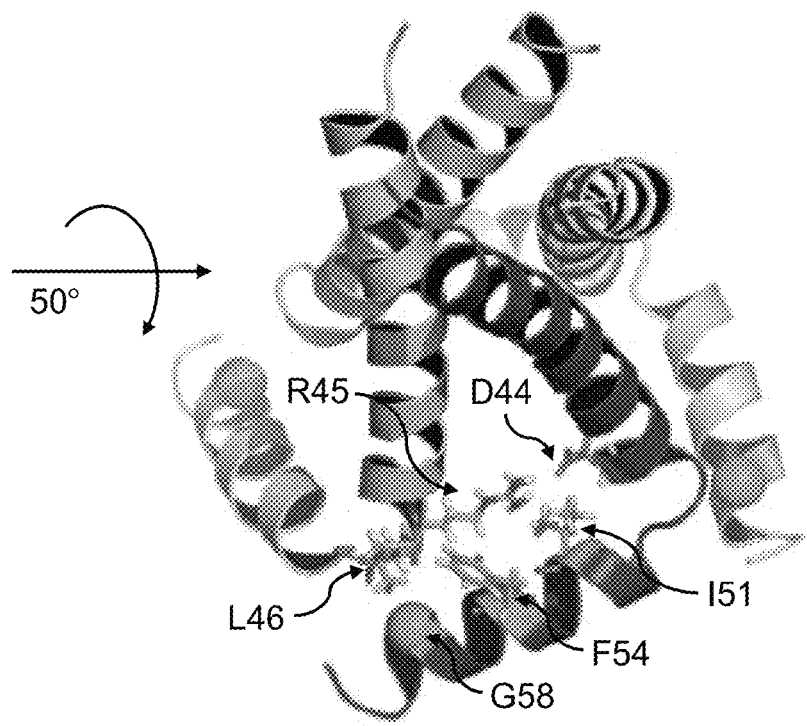
FIG. 7 is a schematic illustration showing several key residues at the junction between the TM and amphipathic helices, including $Gly^{58}$ (shown as Cc, spheres), which facilitates the close approach of adjacent monomers, and $Ile^{51}$ and $Phe^{54}$, which fill a pocket previously described as a rimantadine-binding site

The linewidths of the NMR spectra (FIGS. 25-30) are much narrower for the conductance domain than for the TM domain as described in C. Li, H. Qin, F. P. Gao, T. A. Cross, *Biochim. Biophys. Acta* 1768, 3162 (2007), indicating substantially reduced conformational heterogeneity and higher stability (see also FIG. 24). In the structure determined here, numerous nonpolar residues of the amphipathic helices extend the hydrophobic interactions interlinking the monomers, with their close approach facilitated by the small $Gly^{58}$ (FIG. 7). In particular, $Phe^{48}$ interacts with $Phe^{55}$ and $Leu^{59}$ of an adjacent monomer and $Phe^{54}$ interacts with $Leu^{46}$ of another adjacent monomer.

The starting residues of the amphipathic helix, $Phe^{47}$ and $Phe^{48}$, are a sequence motif known to signal association of the helix with a lipid bilayer as referred to in T. L. Lau, V. Dua, T. S. Ulmer, *J. Biol. Chem.* 283, 16162 (2008). The burial of the hydrophobic portion of the amphipathic helix in the tight internonomer interface is consistent with hydrogen-deuterium exchange data showing it to be the slowest-exchanging region for the full-length protein in a lipid bilayer as described in C. Tian, P. F. Gao, L. H. Pinto, R. A. Lamb, T. A. Cross, *Protein Sci.* 12, 2597 (2003). Furthermore, the $Ser^{50}$ hydroxyl here, which in the native protein is a palmitoylated $Cys^{50}$ residue, is located at an appropriate depth in the bilayer (at the level of the glycerol backbone; see FIG. 4) for tethering the palmitic acid. A third native-like aspect of the amphipathic helix is the outward projection of the charged residues $Lys^{49}$, $Arg^{53}$, $Lys^{60}$ and $Arg^{61}$ (FIG. 4), which conforms to the "positive inside rule" such that M2 interacts favorably with negatively charged lipids in native membranes. The C termini of the amphipathic helices are situated to allow for the subsequent residues of the full-length protein to form the tetrameric MI binding domain. Contrary to the lipid interfacial location determined here, the detergent-solubilized structure has the four amphipathic helices forming a bundle in the bulk aqueous solution where the amides fully exchange with deuterium as referred to in J. R. Schnell, J. J. Chou, Nature 451, 591 (2008).

On the external surface at the C terminus of the TM helix, a hydrophobic pocket, with the $Asp^{44}$ side chain at the bottom, has been described as a binding site for rimantadine as referred to in J. R. Schnell, J. J. Chou, Nature 451, 591 (2008). In the structure of the invention, the large tilt of the TM helices widens the hydrophobic pocket, which is filled by the side chains of $Ile^{51}$ and $Phe^{54}$ in the amphipathic helix, preventing accessibility to the $Asp^{44}$ side chain from the exterior (FIG. 7). Consequently, the formation of a rimantadine-binding site on the protein exterior is likely an artifact of the detergent environment used for that structural characterization.

The heart of acid activation and proton conductance in M2 is the tetrameric $His^{37}$-$Trp^{41}$ cluster, referred to here as the HxxxW quartet as referred to in Y. Tang, F. Zaitseva, R. A. Lamb, L. H. Pinto, *J. Biol. Chem.* 277, 39880 (2002), P. Venkataraman, R. A. Lamb, L. H. Pinto, *J. Biol. Chem.* 280, 21463 (2005) and J. Hu et al., *Proc. Natl. Acad. Sci. U.S.A.* 103, 6865 (2006). The pKa values for the $His^{37}$ residues in the TM domain solubilized in a lipid bilayer were determined as 8.2, 8.2, 6.3, and <5.0 as described in J. Hu et al., Proc. Natl. Acad. Sci. U.S.A. 103, 6865 (2006). At pH 7.5 used in an embodiment of this invention, the histidine tetrad is doubly protonated; each of these two protons is shared between the $N_{\delta 1}$ of one histidine and the $N_{\epsilon 2}$ of an adjacent histidine, giving rise to substantial downfield $^{15}$N chemical shifts and resonance broadening for the protonated sites as referred to in J. Hu et al., *Proc. Natl. Acad. Sci.* U.S.A. 103, 6865 (2006), indicative of a strong hydrogen bond as described in X.-j. Song, A. E. McDermott, *Magn. Reson. Chem.* 39, 537 (2001) and X.-j. Song, C. M. Rienstra, A. E. McDermott, *Magn. Reson. Chem.* 39, 530 (2001).

Figure 12:
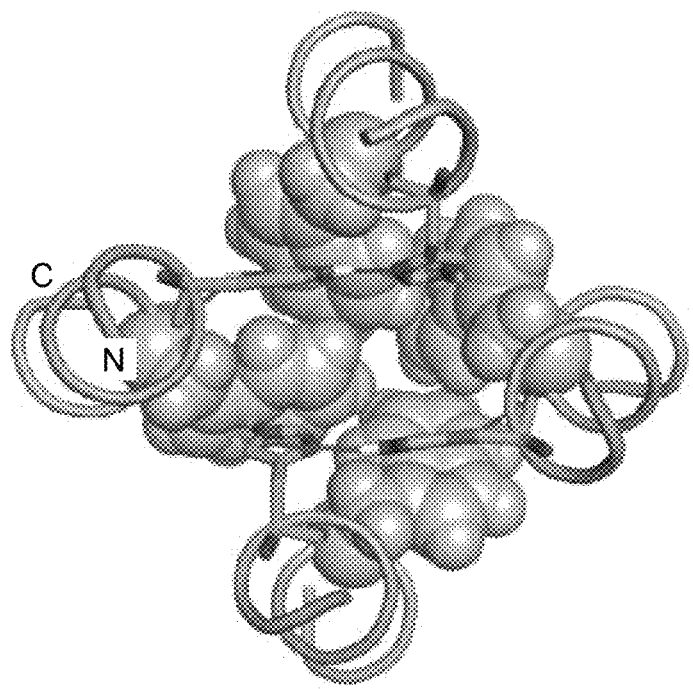
FIG. 12 is a schematic illustration showing the top view of the tetrameric cluster of $H^{37}xxxW^{41}$ ($His^{37}$ as sticks and $Trp^{41}$ as spheres).

The structure of the histidine tetrad as a pair of imidazole-imidazolium dimers is shown in FIG. 12. In each dimer, the shared proton is collinear with the $N_{\delta 1}$ and $N_{\epsilon 2}$ atoms (FIG. 12); the two imidazole rings are within the confines of the backbones, to be nearly parallel to each other—a less energetically favorable situation than the perpendicular alignment of the rings in imidazole-imidazolium crystals and in computational studies as described in A. Quick, D. J. Williams, *Can. J. Chem.* 54, 2465 (1976); J. A. Krause, P. W. Baures, D. S. Eggleston, *Acta Crystallogr. B* 47, 506 (1991) and W. Tatara, M. J. Wojcik, J. Lindgren, M. Probst, *J. Phys. Chem. A* 107, 7827 (2003).

Figure 13:
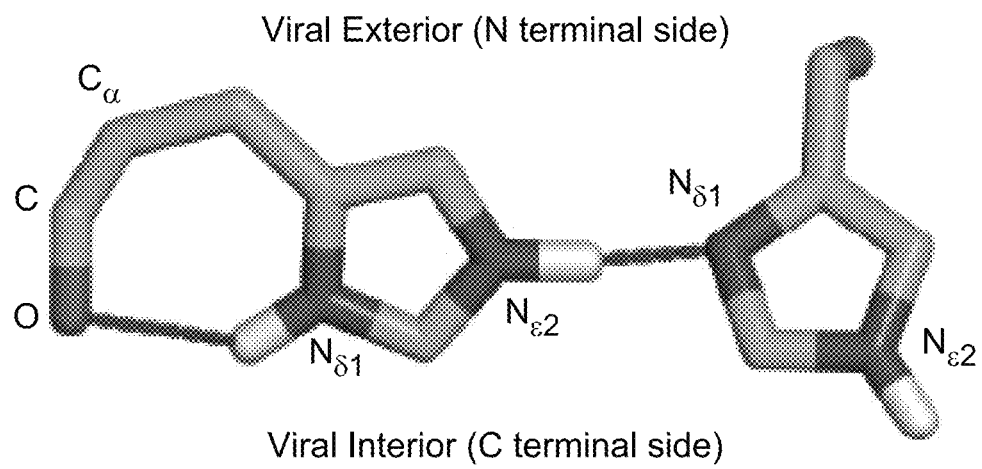
FIG. 13 is a schematic illustration showing the side view of one of the two imidazole-imidazolium dimers.
Figure 20:
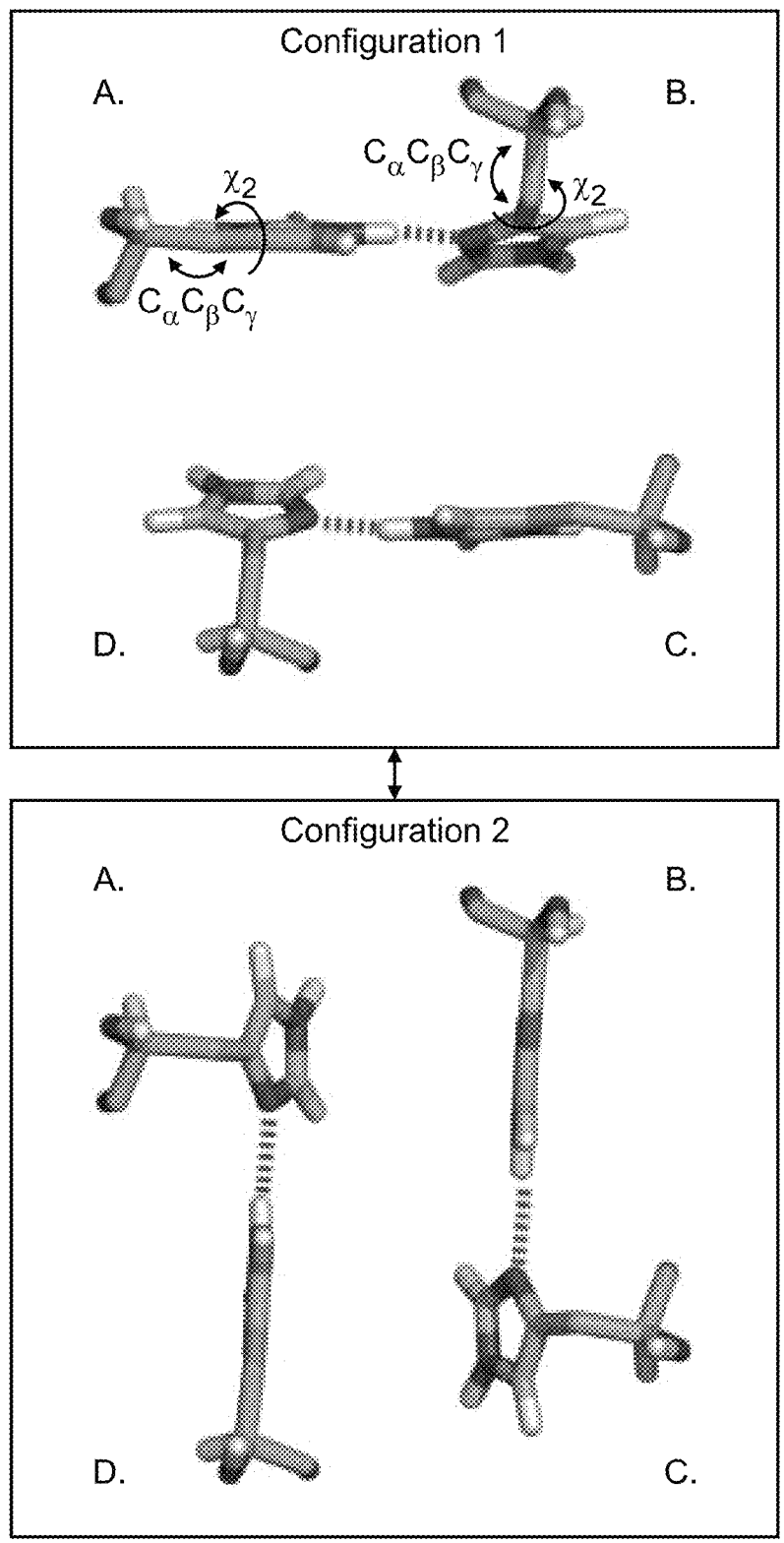
FIG. 20 is a schematic image showing exchange of partners between the two imidazole-imidazolium dimers, leading to apparent C4 symmetry observed by the NMR spectroscopy.

The two $N_{\delta 1}$ and two $N_{\epsilon 2}$ sites of the histidine tetrad not involved in the strong hydrogen bonds are protonated and project toward the C-terminal side (FIGS. 12 and 13). The $N_{\epsilon 2}$ protons interact with the indoles of the Trp$^{41}$ residues (FIG. 12), and the two $N_{\delta 1}$ protons form hydrogen bonds with their respective histidine backbone carbonyl oxygens (FIG. 13). Therefore, in this "histidine-locked" state of the HxxxW quartet, none of the imidazole N—H protons can be released to the C-terminal pore, resulting in a completely blocked channel. Furthermore, the only imidazole nitrogens available for additional protonation are the sites involved in the strong hydrogen bonds; acceptance and release of protons from the N-terminal pore by these sites, coupled with 90° side-chain $\chi 2$ rotations, would allow the imidazole-imidazolium dimers to exchange partners (FIG. 20). That the NMR data show a symmetric average structure suggests that such exchange occurs on a submillisecond time scale.

Figure 21:
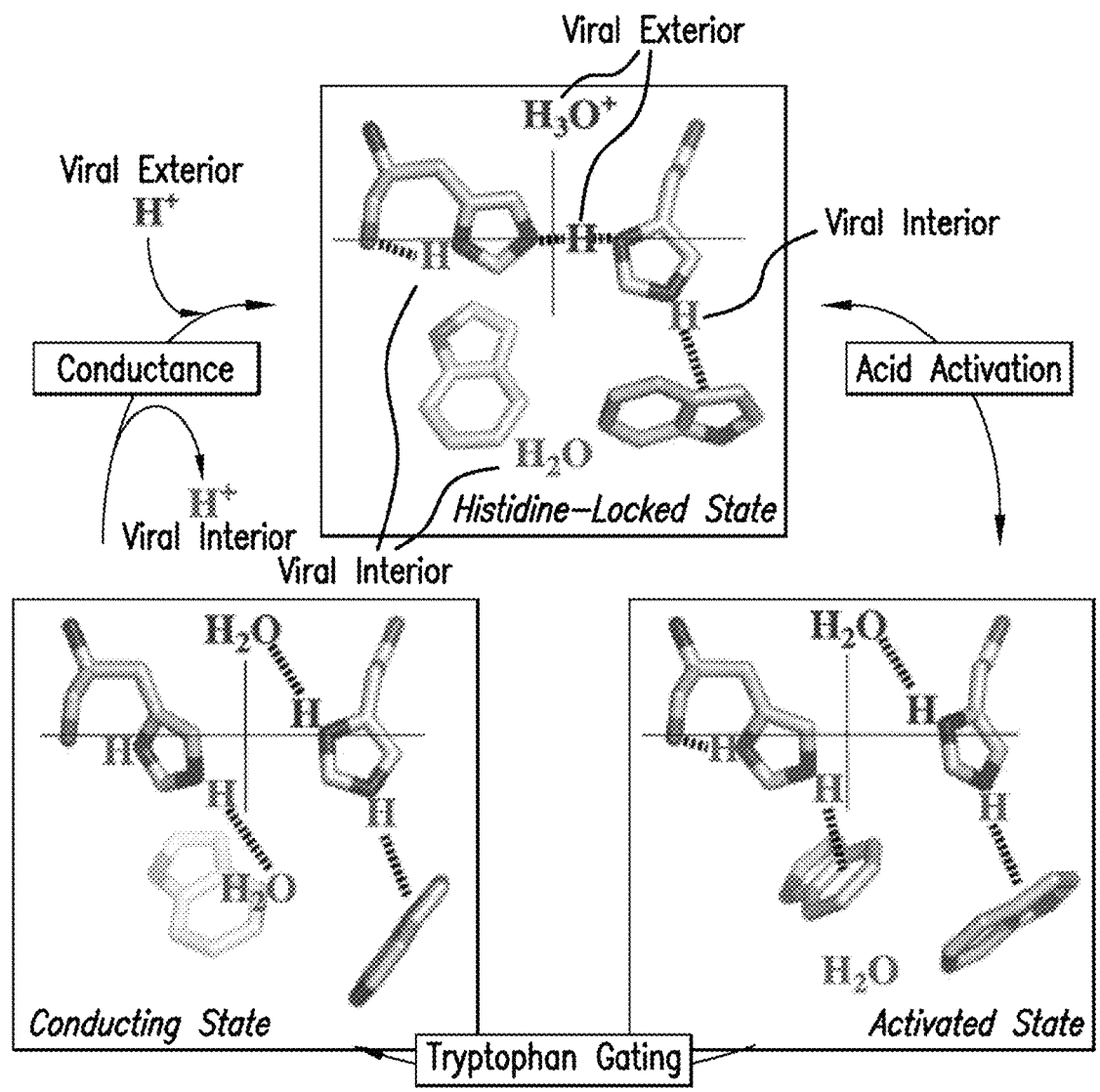
FIG. 21 is a schematic illustration of the a mechanism of acid activation and proton conductance illustrated with half of the HxxxW quartet from a side view.

The structure of the HxxxW quartet at neutral pH suggests a detailed mechanism for acid activation and proton conductance (FIG. 21). Under acidic conditions in the viral exterior, a hydronium ion in the N-terminal pore attacks one of the imidazole-imidazolium dimers. In the resulting "activated" state, the triply protonated histidine tetrad is stabilized by a hydrogen bond with water at the newly exposed $N_{\delta 1}$ site on the N-terminal side and an additional cation-n interaction with a Trp$^{41}$ residue at the $N_{\epsilon 2}$ site on the C-terminal side. Strong cation-π interactions between His$^{37}$ and Trp$^{41}$ were observed by Raman spectroscopy in the TM domain under acidic conditions as described in A. Okada, T. Miura, H. Takeuchi, *Biochemistry* 40, 6053 (2001).

These interactions protect the protons on the C-terminal side from water access. Conformational fluctuations of the helical backbones [in particular, a change in helix kink around Gly$^{34}$ as referred to in M. Yi, T. A. Cross, H, X. Zhou, *Proc. Natl. Acad. Sci.* U.S.A. 106, 13311 (2009)] and motion of the Trp$^{41}$ side chain could lead to occasional breaking of this cation-π interaction. In the resulting "conducting" state, the $N_{\epsilon 2}$ proton becomes exposed to water on the C-terminal side, allowing it to be released to the C-terminal pore. Upon proton release, the histidine-locked state is restored, ready for another round of proton uptake from the N-terminal pore and proton release to the C-terminal pore. In each round of proton conductance, the changes among the histidine-locked, activated, and conducting states of the HxxxW quartet can be accomplished by rotations (<45° change in $\chi_2$ angle) of the His$^{37}$ and Trp$^{41}$ side chains, which are much smaller than those envisioned previously as suggested in L. H. Pinto et al., *Proc. Natl. Acad. Sci.* U.S.A. 94, 11301 (1997), and even less than those needed for the imidazole-imidazolium dimers to exchange partners (FIG. 20).

This mechanism is consistent with many M2 proton conductance observations. The permeant proton is shuttled through the pore via the histidine tetrad, at one point being shared between $N_{\delta 1}$ and $N_{\epsilon 2}$ of adjacent histidines. No other cations can make use of this mechanism, which explains why M2 is proton-selective. With the permeant proton obligatorily binding to and then unbinding from an internal site (i.e., the histidine tetrad), the proton flux is predicted to saturate at a moderate pH on the N-terminal side as described in M. Yi, T. A. Cross, H, X. Zhou, *Proc. Natl. Acad. Sci.* U.S.A. 106, 13311 (2009), which is consistent with conductance observations referred to in I. V. Chizhmakov et al., *J. Physiol.* 494, 329 (1996). Such a permeation model also predicts that the transition to saturation occurs at a pH close to the histidine-tetrad pKa for binding or unbinding the permeant proton.

Indeed, the transition is observed to occur around pH 6 as described in I. V. Chizhmakov et al., *J. Physiol.* 494, 329 (1996), close to the third pKa of the histidine tetrad. Without the histidines, as in the H37A mutant, the proton flux would lose pH dependence, as observed previously in P. Venkataraman, R. A. Lamb, L. H. Pinto, *J. Biol. Chem.* 280, 21463 (2005). Another distinguishing feature of the M2 proton channel is its low conductance, at ~100 protons per tetramer per second (FIGS. 22 and 23) as referred to in J. A. Mould et al., *J. Biol. Chem.* 275, 8592 (2000) and T. I. Lin, C. Schroeder, *J. Virol.* 75, 3647 (2001). Upon acid activation, the HxxxW quartet is primarily in the activated state. Only when the Trp$^{41}$ gate opens occasionally to form the conducting state is the proton able to be released to the C-terminal pore, thus explaining the low conductance.

In the mechanism of this invention, the histidine tetrad senses only acidification of the N-terminal side. This provides an explanation for an observation of Chizhmakov et al. (I. V. Chizhmakov et al., *J. Physiol.* 546, 427 (2003)) when a positive voltage is applied to drive protons outward in M2-transformed MEL cells. A step increase in the bathing buffer pH from 6 to 8 (with the intracellular pH held constant at pH 6) produced a brief increase in outward current, as expected for the added driving force by the pH gradient. The brief increase can be attributed to the release of protons from the triply protonated histidine tetrad to the N-terminal pore (as illustrated by the back arrow from the activated state to the histidine-locked state in FIG. 21) when the pH there is suddenly increased from 6 to 8. With these protons released, the histidine tetrad then becomes doubly protonated and the tryptophan gate becomes closed; however, the outward current quickly decayed to a level lower even than that before the pH increase. In the structure related to the invention, when the pH in the N-terminal side is 8, the HxxxW quartet is stabilized in the histidine-locked state and the Trp$^{41}$ gate prevents excess protons in the C-terminal pore from activating the histidine tetrad. Upon removal of the Trp$^{41}$ gate (e.g., by a W41A mutation), a substantial outward current would be produced, as was observed in Y. Tang, F. Zaitseva, R. A. Lamb, L. H. Pinto, *J. Biol. Chem.* 277, 39880 (2002).

Another embodiment of the invention relates to the observation that the M2 proton channel can be blocked by $Cu^{2+}$ (through His$^{37}$ coordination) applied extracellularly, but not intracellularly as referred to in Y. Tang, F. Zaitseva, R. A. Lamb, L. H. Pinto, *J. Biol. Chem.* 277, 39880 (2002). Again, the triply protonated histidine tetrad stays predominantly in the activated state, in which the Trp$^{41}$ gate blocks $Cu^{2+}$ access to His$^{37}$ from the C-terminal side. However, the W41A mutation opens that access as described in Y. Tang, F. Zaitseva, R. A. Lamb, L. H. Pinto, *J. Biol. Chem.* 277, 39880 (2002).

The structure of the M2 conductance domain solved in liquid crystalline bilayers is consistent which a mechanism for acid activation and proton conductance shown in FIG. 21. This mechanism takes advantage of conformational flexibility, both in the backbones and in the side chains, which arises in part from the weak interactions that stabilize membrane proteins. M2 appears to use the unique chemistry of the HxxxW quartet to shepherd protons through the channel.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be associated with the present invention. The term "recombinant" means a nucleotide sequence that has been manipulated "by man" and that does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized: for example, the codons may be optimized for human use. In preferred embodiments the nucleotide sequences of the invention are both mutated to abrogate the normal in vivo function of the encoded proteins, and codon optimized for human use.

As regards codon optimization, the nucleic acid molecules associated with the invention have a nucleotide sequence that may encode the antigens and can be designed to employ codons that are used in the genes of the subject in which the antigen is to be produced. In a preferred embodiment, the codons used are "humanized" codons, i.e., the codons are those that appear frequently in highly expressed human genes as described in Andre et al., "Increased immune response elicited by DNA vaccination with a synthetic gp120 sequence with optimized codon usage," *J. Virol.* 72:1497-1503 (1998). Any suitable method of codon optimization may be used. Such methods, and the selection of such methods, are well known to those of skill in the art. In addition, there are several companies that will optimize codons of sequences, such as Geneart and its website of the same name. Thus, the nucleotide sequences utilized in the invention can readily be codon optimized.

Another embodiment of the invention also encompasses nucleotide sequences that encode proteins, peptides or small molecules or the functional and/or equivalent variants and derivatives of the proteins, peptides or small molecules that may bind to the histidine tetrad of the M2 protein based on the structural information provided by the invention to affect virus function. For instance, changes in a DNA sequence that do not change the encoded amino acid sequence, as well as those that result in conservative substitutions of amino acid residues, one or a few amino acid deletions or additions, and substitution of amino acid residues by amino acid analogs are those that will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the proteins, peptides or small molecules of interest.

For purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin et al., "Methods for assessing the statistical significance of molecular sequence features by using general scoring schemes" *Proc. Natl. Acad. Sci.* 87: 2264-68 (1990), modified as in Karlin et al., "Applications and statistics for multiple high-scoring segments in molecular sequences," *Proc. Natl. Acad. Sci.* 90: 5873-77 (1993).

Another example of a mathematical algorithm used for comparison of sequences is the algorithm of Myers et al., "Optimal alignments in linear space," *CABIOS* 4: 11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson et al., "Improved tools for biological sequence comparison," *Proc. Natl. Acad. Sci.* 85: 2444-48 (1988).

Advantageous for use according to the present invention is the WU-BLAST (Washington University BLAST) version 2.0 software. WU-BLAST version 2.0 executable programs for several UNIX platforms can be downloaded from on-line. This program is based on WU-BLAST version 1.4, which in turn is based on the public domain NCBI-BLAST version 1.4 described in Altschul et al., "Local alignment statistics," *Methods in Enzymology*, Doolittle ed., 266: 460-80 (1996); Altschul et al., *J. Mol. Biol.*, 215: 403-410 (1990); Gish et al., *Nature Genetics* 3: 266-272 (1993); and Karlin et al., *Proc. Natl. Acad. Sci.* 90: 5873-5877 (1993), the entire contents and disclosures of which are incorporated herein by reference.

The various recombinant nucleotide sequences and polypeptides associated with the invention are made using standard recombinant DNA and cloning techniques. Such techniques are well known to those of skill in the art. See, for example, Sambrook et al., *Molecular Cloning: A Laboratory Manual*, second edition, volume 1, 2 and 3 (1989).

In certain embodiments, the polypeptides associated with the present invention may be used in vitro (such as using cell-free expression systems) and/or in cultured cells grown in vitro in order to produce the polypeptides which may then be used for various applications such as in the production of proteinaceous vaccines. For applications where it is desired that the polypeptides be expressed in vivo, for example when the transgenes of the invention are used in DNA or DNA-containing vaccines, any vector that allows for the expression of the polypeptides of the present invention and is safe for use in vivo may be used.

For the polypeptides associated with the present invention to be expressed, the protein coding sequence may be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto.

In another embodiment, the invention provides a method of designing or identifying a drug candidate, small molecule inhibitor, an inhibitor compound of an influenza A virus based on computational methods using the structure and its coordinates, wherein the inhibitor binds at least one residue within the histidine tetrad to adversely affect viral function. The design method may be facilitated by using NMR spectra of samples of M2 protein fragments or equivalent constructs thereof. The method may further include the step of optimizing the design of the molecule that may be able to bind to further residues within the structure to affect viral function using methods which include but are not limited to NMR, particularly solid state NMR, X-ray crystallography, synthetic chemistry and combinations thereof.

Another embodiment of the invention is a method of designing an inhibitor compound that may modify the tetrameric His37-Trp41 cluster, referred to here as the HxxxW quartet, or any substructure, based on its conformation to rationally design one or more small molecule inhibitors.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

The description of the present invention is enhanced by the various examples that follow.

Example 1

Cloning, plasmid construction, expression, and purification. Cloning, plasmid construction, protein expression and purification followed a previously published procedure as described in J. Hu et al., *Protein Sci.* 16, 2153 (2007). Briefly, the DNA corresponding to M2 residues 22-62 of influenza A Udorn/1972 virus is amplified by PCR and cloned into a modified pET30 vector containing a TEV protease cleavable MBP fusion protein expression system by ligation-independent cloning. The plasmid encoding the MBP-TEVc-M2 (22-62) fusion protein is transformed into *E. coli* strain BL21 (DE3)-RP codon plus for expression. A single colony is picked and inoculated into 3-mL LB media with 100 µg/mL ampicillin, and grown overnight at 37° C. with shaking. Cells are then collected by centrifugation, washed with M9 media once, and inoculated into 1-L M9 media with stable isotope labels (described below). The culture is grown to an $OD_{600}$=0.6 at 37° C. with shaking, and cooled to 30° C. Finally expression is induced with 0.4 mM IPTG for 12-16 h at 30° C. with shaking.

For purification, cells expressing the fusion protein are collected by centrifugation at 4000 g for 10 min, and then washed once with a buffer containing 20 mM Tris-HCl (pH 8.0). Cooled cells are lysed by a French press in a binding buffer containing 50 mM NaCl and 20 mM Tris-HCl (pH 8.0), and the supernatant is collected after centrifugation at 10,000 g for 20 min. DDM is then added to the supernatant to a final concentration of 0.87% to solubilize the fusion protein in the membrane fraction. The supernatant is allowed to incubate with $Ni^{2+}$-NTA agarose resin (Qiagen) while gently shaking. After binding at 4° C. overnight, the resin is washed with a binding solution containing 20 mM imidazole followed by elution with a buffer containing 50 mM NaCl, 20 mM Tris-HCl (pH 8.0), 0.087% DDM, and 300 mM imidazole. The fractions containing the fusion protein are pooled and stored at 4° C.

To cleave the fusion protein, TEV is added to the freshly purified fusion proteins (2.5-5 mg/mL) at a mass ratio of 1:10. The TEV cleavage reaction takes place at room temperature for 16-20 h. To purify the M2 conductance domain, the TEV cleavage reaction is stopped by addition of TCA at a final concentration of 6%. The precipitate is collected by slow centrifugation. After washing the pellet with water twice to remove residual TCA, the protein is lyophilized in a vacuum centrifuge. Then 20 mL of methanol is added per liter of culture and mixed gently for several hours at room temperature. To remove the undissolved proteins (MBP and TEV), the solution is centrifuged at 13,000 g for 20 min, and the supernatant is carefully collected. The M2 protein is then lyophilized in a vacuum centrifuge and stored at −20° C.

The purified protein, after being solubilized in DDM micelles, appears as a band in SDS-PAGE gel at ~22 kDa (FIG. 24), which is close to the molecular weight of the M2 conductance domain as a tetramer.

For uniform $^{15}N$ labeling, M9 media is supplemented with 1 g of $^{15}N$-ammonium chloride. For amino-acid specific $^{15}N$ labeling, all 20 but the amino acid to be labeled are added per liter of M9 media in the following amounts: 800 mg each of Asp and Glu; 500 mg each of Ala, Val, Leu, and Ile; and 200 mg each of the other amino acids. The amount of the $^{15}N$ labeled amino acid is 100 mg per liter of M9 media. Alternatively, to M9 media containing $^{15}N$-ammonium chloride unlabeled amino acids in the amounts listed above are added to prevent their labeling (known as reverse labeling). Labeling efficiency and cross-labeling are checked by comparing the solution NMR heteronuclear single quantum coherence spectra of uniformly labeled, specific amino-acid labeled, and reverse labeled proteins in LPPG detergent micelles.

Example 2

Uniformly aligned sample preparation. Solid supported lipid-bilayer samples containing the M2 conductance domain are prepared as follows. DOPC and DOPE phospholipids are obtained from Avanti Polar Lipids as chloroform solutions. Aliquots of lipids in chloroform are mixed in a molar ratio of 4:1 (DOPC:DOPE) in a glass vial and thoroughly dried under flow of nitrogen gas to form a thin translucent film 5 mg of peptide in 10 ml TFE:methanol (1:1) is added to a DOPC: DOPE film (~75 mg total weight) and vortexed to solubilize the film. Organic solvents are removed by flowing nitrogen gas gently. Residual solvent is removed under vacuum for several hours. The resulting translucent protein-lipid film is hydrated with a small volume (~5 ml) of 10 mM Tris-HCl (pH 7.5), vortexed, and mixed in a shaker bath at 37° C. for 3 hours. The lipid suspension is then transferred to a 1 kDa MW cutoff dialysis bag. The dialysis bag is placed in 1 L of 5 mM Tris-HCl buffer (pH 7.5) overnight to equilibrate the pH between the M2 liposomes and the buffer and to remove any trace amount of organic solvents. The liposomes are pelleted by ultracentrifugation at 196,000 g. The pellet is agitated at 37° C. for 1 h until fluid. This thick fluid is spread onto 40 glass slides (5.7 mm×12 0 mm) (Marienfeld Glassware, Bad Margentheim, Germany) and dehydrated in a 70-75% humidity chamber. The dehydrated slides are rehydrated with 1.5 µl of 2 mM Tris-HCl buffer (pH 7.5) and then stacked into a rectangular glass cell (New Era Enterprises Inc). The stacked slides are incubated at 43° C. for 48 h in a 96% relative humidity (saturated $K_2SO_4$) chamber, resulting in uniformly aligned samples.

Example 3

For NMR spectroscopy, samples are prepared with $^{15}N$-Leu, $^{15}N$-Ile, $^{15}N$-Val, $^{15}N$-Ala, and $^{15}N$-Phe labeling as well as uniform $^{15}N$ labeling and reverse labeling. All NMR experiments are performed on 600 MHz wide bore and 900 MHz ultra wide bore spectrometers at the National High Magnetic Field Laboratory. All spectra are obtained at 30° C. and pH 7.5 using home-built low-E static NMR probes as described in P. L. Gor'kov et al., *J. Magn. Reson.* 185, 77 (2007). The polarization inversion spin exchange at magic angle (PISEMA) and SAMPI4 pulse sequences were used for measuring correlation spectra in the $^{15}N$ chemical shift and $^{15}N$-$^{1}H$ dipolar coupling dimensions (as described in A. Ramamoorthy, S. J. Opella, *Solid State Nucl. Magn. Reson.* 4, 387 (1995) and A. A. Nevzorov, S. J. Opella, *J. Magn. Reson.* 164, 182 (2003)). Typical experimental settings were as follows: the RF field strength is 50 kHz for cross polarization and 62.5 KHz for decoupling; the durations of contact pulse and 90° pulse were 800 µs and 4 µs, respectively; 4000 scans were acquired for each of 16 increments in the dipolar coupling dimension for $^{15}N$ chemical shifts >125 ppm and 32 increments for $^{15}N$ chemical shifts <125 ppm.

Figure 25:
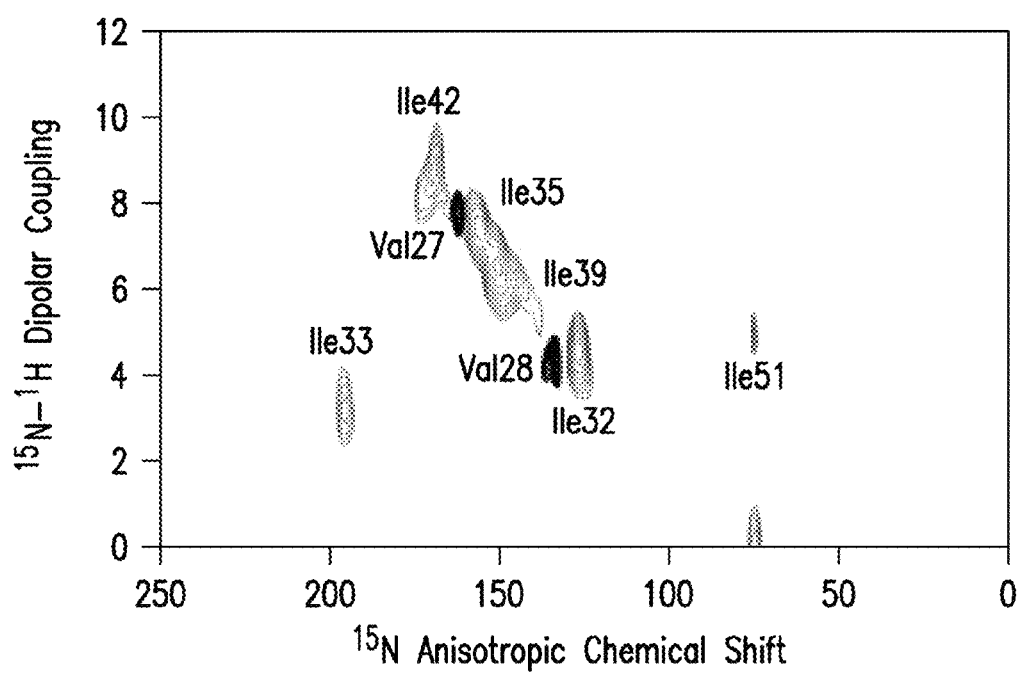
FIG. 25 is a graph showing the spectral superposition of $^{15}$N-Ile (blue) and $^{15}$N-Val (black) labeled samples.

Resonances of amino acids with the lowest frequencies of occurrence in the M2(22-62) sequence were assigned first, based on spectra of specific amino-acid labeled samples and according to the resonance pattern and geometry of helices as referred to in F. M. Marassi, S. J. Opella, *J. Magn. Reson.* 144, 150 (2000) and J. Wang et al., *J. Magn. Reson.* 144, 162 (2000). In particular, $^{15}N$ resonances of residues in a helix trace a polarity index slant angle (PISA) wheel analogous to a helical wheel. Due to helical periodicity, resonances of residues at i, i+4, and i+7 positions appear close together on the PISA wheel. Accordingly, two Val resonances were identified in sequential positions on a PISA wheel, and assigned to $Val^{27}$ and $Val^{28}$ (FIG. 25). The Ile resonance closest to $Val^{28}$ is assigned to $Ile^{32}$ since they are i to i+4 related. The next residue along the sequence is also an Ile; a lone Ile resonance is indeed found at a location on the PISA wheel expected for the sequential nearest neighbor and hence assigned to $Ile^{33}$. The resonance pattern of these Val and Ile residues is similar to that found previously for the transmembrane domain (as referred to J. Hu et al, *Biophys. J.* 92, 4335 (2007)), suggesting that the N-terminal half of the transmembrane helix in the conductance domain has similar helix tilt and rotation as in the transmembrane domain. This similarity allowed the assignment of the $Leu^{26}$ resonance.

All of the Phe resonances, including $Phe^{47}$, are clustered below 125 ppm in $^{15}N$ chemical shifts (FIG. 26), consistent with them being associated with a lipid-interface bound helix, i.e., the amphipathic helix (C. Tian, P. F. Gao, L. H. Pinto, R. A. Lamb, T. A. Cross, Protein Sci. 12, 2597 (2003); N. J. Traaseth et al., Proc. NatL Acad. Sci. USA 104, 14676 (2007) and R. Fu, E. D. Gordon, D. J. Hibbard, M. Cotten, J. Am. Chem. Soc. 131, 10830 (2009)). There is one Leu and one Ile resonance each below 125 ppm (FIGS. 25 and 26), which are assigned to $Leu^{59}$ and $Ile^{51}$, respectively, and are presumed to be part of the PISA wheel for the amphipathic helix. Three Phe resonances are tightly clustered on this PISA wheel, but the fourth Phe resonance, located away from the PISA wheel, is assigned to $Phe^{47}$. The Phe resonance closest to the $Leu^{59}$ resonance is assigned to $Phe^{55}$ (i+4 to i related); the next nearest Phe resonance is assigned to $Phe^{48}$ (i+7 to i related); and the last Phe resonance is assigned to $Phe^{54}$. That the resonances of these residues were clustered on the PISA wheel is an indication that the amphipathic helix extended over them.

Figure 27:
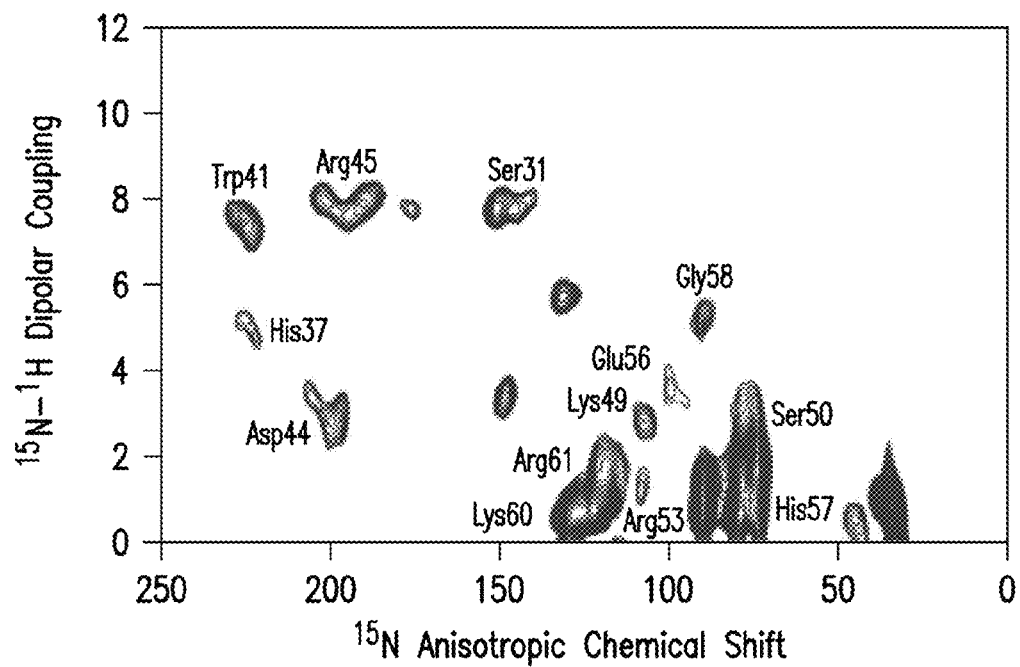
FIG. 27 is a graph showing the spectra of a reverse $^{15}$N labeled sample. Data for TM and amphipathic helices were acquired with different proton offsets.
Figure 28:
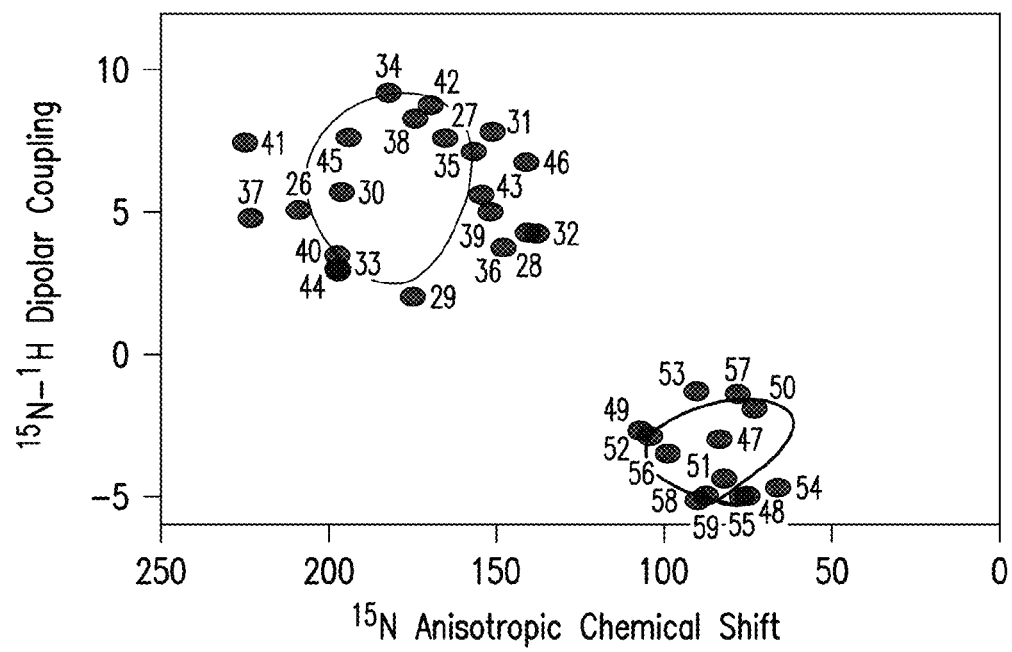
FIG. 28 is a graph showing the PISEMA resonance positions of the protein.

After the assignment of 2 Val (out of 2), 3 Ile (out of 6), 2 Leu (out of 7), and 4 Phe (out of 4) residues, the remaining resonances were grouped into either the transmembrane helix or amphipathic helix (according to whether $^{15}N$ chemical shifts were >125 ppm). These two sets of resonances were separately assigned by the PIPATH program, which was developed by Asbury et al. (T. Asbury et al, *J. Magn. Reson.* 183, 87 (2006)) for resonance assignment of membrane helices. The resonance assignments of the other residues of the M2 conductance domain are found in FIGS. 25-27. The PISA wheel of the amphipathic helix is consistent with it being tilted at 15° with respect to the bilayer surface, as demonstrated by fitting to a simulated PISA wheel for an ideal helix (FIG. 28). That the hydrophobic residues had larger dipolar couplings (FIGS. 25 and 26) than the positively charged residues (FIG. 27) defined the C-terminal of the amphipathic helix as being tilted away from the bilayer center. Evidently, the transmembrane helix and the amphipathic helix is connected by a tight turn, since the intervening residue, $Phe^{47}$, is quite rigid, as indicated by its significant dipolar coupling (−3 kHz) and anisotropic chemical shift (−70 ppm).

Example 4

Figure 26:
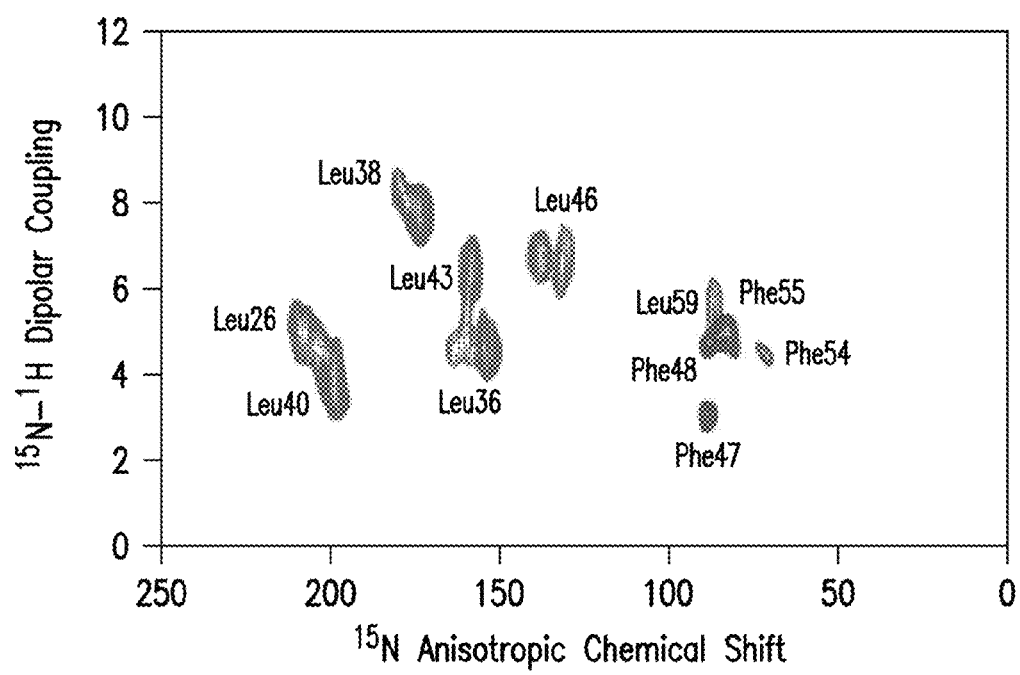
FIG. 26 is a graph showing the spectral superposition of $^{15}$N-Leu (green) and $^{15}$N-Phe (red) labeled samples.

Structure calculations. As noted above, the tetrameric state of the M2 conductance domain is demonstrated by SDS-PAGE electrophoresis (FIG. 24). That the tetramer is symmetric is demonstrated by the observation of a single resonance for each residue (FIGS. 25-27). Using the peak positions of these resonances (FIG. 28) as restraints, the final tetrameric structure is calculated in four steps. First, a structure for a monomer is generated through simulated annealing. Second, a preliminary structure for the tetramer is assembled by simulated annealing. Third, the tetramer structure is refined by restrained molecular dynamics simulations in a hydrated lipid bilayer. Finally, the sidechains of the HxxxW quartet were optimized by quantum chemical calculations. Below, these steps are described in more detail.

Monomer structure. An M2(22-62) monomer structure is generated using Xplor-NIH (as described in C. D. Schwieters, J. J. Kuszewski, N. Tjandra, G. M. Clore, J. Magn. Reson. 160, 65 (2003)) in torsion-angle space. Starting with an extended conformation, a monomer is equilibrated at 3500 K for 20 ps, with the backbone torsion angles of residues 26-46 and 48-58 restrained to ideal membrane helix values ($\phi$=−65° and $\psi$=−40° by flat-well (±30°) potentials (force constant at 5 kcal/mol/rad2). Simulated annealing is then started, with the temperature of the monomer decreasing from 3500 K to 100 K with decrements of 25 K per 2 ps. Restraints to the PISEMA peak positions are enforced for residues 26-59 by flat-well (±10 ppm in chemical shifts and ±0.5 kHz in dipolar couplings) harmonic potentials, with the force constants gradually increasing from 0.00006 to 12 kcal/mol/ppm2 for chemical shifts and 0.00003 to 6 kcal/mol/kHz2 for dipolar couplings. Additionally, the backbone torsion angles of residues 26-46 and 48-58 are again restrained to ideal membrane helix values by flat-well harmonic potentials (force constant at 200 kcal/mol/rad2); the distances between i and i+4 backbone hydrogen bonding atoms (carbonyl oxygen and amide nitrogen) of these residues were further restrained with flat-well ($\pm 0.3$ Å) harmonic potentials, with the force constant increasing from 1 to 30 kcal/mol/Å2. Energy terms for bond angles, improper dihedral angles, and van der Waals interactions are scaled gradually from 0.4 to 1, 0.02 to 4, and 0.1 to 1, respectively (no scaling of the energy term for bond lengths) Finally the monomer is subjected to 2000 steps of energy minimization. The above procedure is repeated to generate 300 monomer structures. The top 10 structures all had well-defined TM and amphipathic helices, with average deviations from PISEMA restraints at 0.2 kHz for dipolar couplings and 3 ppm for chemical shifts. The structure with the least violations of the PISEMA restraints is used below to build a tetramer.

Preliminary tetramer structure. A tetramer is manually built by duplicating the monomer three times and positioning the four copies around a central axis with C4 symmetry. Each copy is oriented such that the polar residues, $Ser^{31}$, $His^{37}$, $Trp^{41}$, $Asp^{44}$, and $Arg^{45}$ of the transmembrane helix faced the central axis. Starting from the manually built tetramer, 20 structures are generated by running the Xplor-NIH program (C. D. Schwieters, J. J. Kuszewski, N. Tjandra, G. M. Clore, *J. Magn. Reson.* 160, 65 (2003)) following a procedure consisting of five stages: (1) equilibration at 2000 K for 2000 steps; (2) simulated annealing from 2000 K to 20 K with decrements of 10 K per 1000 steps; (3) energy minimization for 500 steps; (4) simulated annealing from 2000 K to 0 K with decrements of 10 K per 1000 steps; and (5) energy minimization for 500 steps. The tetramer is represented by torsion angles in stages (1)-(3) and by Cartesian coordinates in stages (4)-(5). In addition to the energy terms and PISEMA and helix restraints used in monomer building, the following inter-monomer restraints are introduced to maintain the tetrameric state and ensure that the polar residues of the transmembrane helices faced the pore: $Ser^{31}$ $O_\gamma$-L26' O, $His^{37}N_{\delta 1}$- Trp41' $N\epsilon_2$, His37' $N\epsilon_2$-His37' $N_{\delta 1}$, and Arg45 Cξ Asp44' Cγ [flat-well ($\pm 0.2$ Å) harmonic potentials centered at 3 Å with force constant of 100 kcal/mol/Å$^2$]. The amphipathic helices are also loosely restrained by using distance information obtained by EPR on a similar construct (residues 23-60) as referred to in P. A. Nguyen et al., *Biochemistry* 47, 9934 (2008)) [flat-well ($\pm 2$ Å) symmetric cubic potentials centered at 17-23 Å between Cβ atoms of the same residue on adjacent monomers, for residues 49-57, with force constant ramped from 0.00001 to 10 kcal/mol/Å$^3$]. C4 symmetry is enforced by requiring equal distances from the central axis to each monomer, adapting protocols developed previously (M. Nilges, *Proteins* 17, 297 (1993) and S. I. O'Donoghue, G. F. King, M. Nilges, *J. Biomol. NMR* 8, 193 (1996)) with force constant 1000 kcal/mol/Å$^2$.

The amphipathic helix is connected to the TM helix by a tight turn involving just 2 peptide planes. The PISEMA restraints fixed the peptide planes with high precision with respect to the bilayer normal and significantly limited the choices of the backbone torsion angles. The EPR restraints (as described in P. A. Nguyen et al, *Biochemistry* 47, 9934 (2008)) further narrowed the conformational space and allowed the orientation of the amphipathic helix in the bilayer plane to be well defined. The 20 tetramer structures produced consisted of a major population with a "clockwise" orientation for the amphipathic helices and a minor population with a "counterclockwise" orientation. The structure with the least violations of the PISEMA restraints and representing the major population is selected for further refinement, as described next.

Refinement of tetramer structure by restrained molecular dynamics simulations. The preliminary tetramer structure is placed in a DOPC:DOPE bilayer pre-equilibrated in TIP3P waters. The preparation of the bilayer system started with a structure file of a DOPC bilayer (128 lipids per leaflet) downloaded from a CHARMM-GUI (further information is available on the website of CHARMM-GUI) (as described in S. Jo, T. Kim, W. Im, *PLoS One* 2, e880 (2007)). From each leaflet, 3 lipids are randomly selected for removal and another 25 are randomly selected for replacement by DOPE, resulting in a bilayer with 200 DOPC and 50 DOPE lipid molecules. The DOPC:DOPE ratio, 4:1, reproduces the composition of the lipid bilayer used for the NMR spectroscopy. The bilayer is solvated by 10985 water molecules (44 water molecules per lipid), and the lipid-water system is further equilibrated for 30 ns by NAMD as referred to in J. C. Phillips et al., *J Comput Chem* 26, 1781 (2005), under constant normal pressure, surface area, and temperature (NPZAT ensemble) at 1 bar, 8425 A2, and 303.15 K, respectively. The surface area is chosen to reproduce the area per lipid, 67.4 A2, observed experimentally for liquid crystalline DOPC bilayers as further described in N. Kucerka et al., *Biophys J* 95, 2356 (2008).

After placing the preliminary structure into the DOPC:DOPE bilayer, lipid and water molecules overlapping with the protein molecule are removed, resulting in 152 DOPC lipids, 37 DOPE lipids, and 10870 water molecules. To mimic the pH used for the NMR spectroscopy, two of the $His^{37}$ residues are neutral and the other two are protonated. To neutralize the whole system, 10 chloride ions are added.

After 500 steps of energy minimization, the simulation system is equilibrated under constant temperature and pressure conditions for 1 ns. During the energy minimization and equilibration, residues 24-46 and 51-58 are restrained to form ideal membrane helices by harmonic potentials on backbone hydrogen bond distances (force constant at 50 kcal/mol/Å$^2$) and dihedral angles (force constant at 100 kcal/mol/rad$^2$); C4 symmetry of the tetramer is enforced by applying distance restraints between the corresponding Cα atoms of adjacent monomers (force constant at 50 kcal/mol/Å$^2$). After the equilibration, the PISEMA restraints are gradually introduced by increasing the force constants to 0.02 kcal/mol/ppm$^2$ and 1.0 kcal/mol/kHz$^2$ over a simulation time of 0.5 ns. At this point the helix restraints are removed, and the PISEMA restraint force constants are gradually increased up to 0.9 kcal/mol/ppm$^2$ and 12.0 kcal/mol/kHz$^2$ while maintaining the C4-symmetry restraint. In order to stabilize the simulation with the greater PISEMA restraint force constants, the masses of backbone N, HN, and C atoms of residues 26 to 59 are increased to 30 atomic units. This last phase of the simulation lasted 0.1 ns, from which the snapshot with the best fit to the PISEMA data is selected. After fixing the backbone, the sidechains are further refined by continuing the simulation for 1 ns.

The refinement by restrained molecular dynamics simulations is performed by NAMD 2.7 (as described in J. C. Phillips et al., *J Comput Chem* 26, 1781 (2005).) using the CHARMM27 force field with the CMAP correction (A. D. MacKerell et al., *Journal of Physical Chemistry B* 102, 3586 (1998) and A. D. Mackerell, M. Feig, C. L. Brooks, *Journal of Computational Chemistry* 25, 1400 (2004).). The particle-mesh Ewald summation method is used to treat long-range electrostatic interactions (A. Toukmaji, C. Sagui, J. Board, T. Darden, *Journal of Chemical Physics* 113, 10913 (2000)). An integration time step of 1 fs is used with a multiple timestepping algorithm (T. Schlick et al., *Journal of Computational Physics* 151, 9 (1999)). Bonded interactions were calculated every time step, with short-range non-bonded interactions calculated every second time step, and long range (>12 Å) electrostatic interactions calculated every fourth time step. Van der Waals interactions were switched off smoothly between 10 and 12 Å. The pair list of non-bonded interactions is updated every 10 steps with a 13.5 Å cutoff Pressure is maintained by the Nose-Hoover Langevin piston method at 1 bar with a constant ratio of x-y dimensions of the periodic boundary (G. J. Martyna, D. J. Tobias, M. L. Klein, *Journal of Chemical Physics* 101, 4177 (1994) and S. E. Feller, Y. H. Zhang, R. W. Pastor, B. R. Brooks, *Journal of Chemical Physics* 103, 4613 (1995)). Temperature is maintained at 303.15 K using Langevin dynamics with 1.0 ps$^{-1}$ damping coefficient. PISEMA, helix, and C4-symmetry restraints were implemented into NAMD using the TCL force interface.

Sidechain optimization of HxxxW quartet by quantum chemical calculations. Current force fields do not model well the unique structure of the HxxxW quartet. Instead quantum chemical calculations are used to optimize the sidechains of the quartet. The system is comprised of residues His$^{37}$, Leu$^{38}$, Leu$^{40}$, and Trp$^{41}$, with the starting conformation taken from the molecular-dynamics refined structure. The ONIOM protocol (S. Dapprich, I. Komaromi, K. S. Byun, K. Morokuma, M. J. Frisch, *Journal of Molecular Structure-Theochem* 462, 1 (1999)) is used to accommodate the relatively large system for the quantum calculations. Briefly, the system is divided into two layers. The inner layer, comprised of all the His$^{37}$ and Trp$^{41}$ sidechains (excluding $C_\beta$ and $H_\beta$ atoms), is treated by B3LYP/6-31G**. The outer layer, comprised of the rest, is treated by the AM1 semiempirical method. The system is optimized with all the backbone heavy atoms fixed. These calculations were done using the Gaussian 03 package (M. J. Frisch et al. (Gaussian, Inc., Wallingford, Conn., 2004)).

The optimized sidechain conformation of the HxxxW quartet is uniquely determined, as optimizations starting from different initial conformations and using somewhat different protocols always result in the same final conformation. This conformation features two strong hydrogen bonds between histidine $N^{\delta 1}$ and $N^{\epsilon 2}$ atoms. Importantly, calculated NMR chemical shifts of these nuclei are in good agreements with those measured on the M2 transmembrane domain at pH 7 (J. Hu et al., *Proc. Natl. Acad. Sci.* USA 103, 6865 (2006)).

The final structure of the conductance domain is produced by replacing the HxxxW quartet of the molecule-dynamics refined structure by the ONIOM-optimized conformation and energy-minimizing the rest of the simulation system while imposing the PISEMA and C4-symmetry restraints (the latter force constant now at 100 kcal/mol/Å$^2$). The backbone $^{15}$N chemical shifts and $^{15}$N-$^{1}$H dipolar couplings calculated on the final structure agree very well with the PISEMA data (FIGS. 29 and 30); the deviations are 6 ppm and 0.4 kHz, well within the respective experimental errors of 10 ppm and 0.5 kHz. In addition, $^{15}$N data obtained from the His$^{37}$ and Trp$^{41}$ sidechains in the M2™ domain as described in K. Nishimura, S. Kim, L. Zhang, T. A. Cross, *Biochemistry* 41, 13170 (2002) and R. Witter et al., Proc. WSEAS: *Biochem. Med. Chem.*, in press (2010) is consistent with the refined sidechain geometry of the conductance domain described here.

To generate an ensemble of structures, the process starting from the 0.5-ns simulation in which the PISEMA restraints are gradually introduced to the end is repeated. Eight structures are generated, which had average RMSD of 0.6 A calculated over backbone heavy atoms. These structures have been deposited in the Protein Data Bank with accession code 2L0J.

Example 5

Conductance measurements. The M2 conductance domain is characterized functionally using the liposome proton uptake assay (as described in T. I. Lin, C. Schroeder, *J. Virol.* 75, 3647 (2001) and J. C. Moffat et al., *Biophys J* 94, 434 (2008).). The M2-containing liposomes (145 nm in diameter) are prepared from a solution of 5 pM tetramer and 20 mg/ml bacterial polar lipids (Avanti Polar Lipids) in an "internal" buffer (50 mM KCl, 50 mM $K_2HPO_4$, 50 mM $KH_2PO_4$, pH 8.0, 320 mOsm) using a procedure similar to that described under "Uniformly aligned sample preparation". Namely, protein and lipid are cosolubilized in methanol and chloroform, dried to a thin film under a N2 stream and then vacuum, taken up in internal buffer, then thrice frozen, thawed, and sonicated. The liposome suspension is then passed 21 times through a polycarbonate filter (Avestin, Ottawa, Canada) at 50-60° C., and evaluated with dynamic light scattering. Conductance measurements are started by diluting the liposomes 100-fold into an "external" buffer (165 mM NaCl, 1.67 mM sodium citrate, 0.33 mM citric acid, 320 mOsm, titrated appropriately for the target pH,) at room temperature (21° C.). One minute later, the pH is fine tuned by titration. Two minutes thereafter, valinomycin is added (to 30 nM) to allow electrostatic compensation of proton flow and hence proton uptake, and the development of a membrane potential, nominally at −114 mV.

Proton uptake is calculated from the pH change of the external buffer, as measured by an electrode. The pH measurements are calibrated after the vesicles are completely depolarized (using CCCP) by the average of two injections of 30 nEq HCl each. Corrections are made for baseline H$^+$ leakage into the liposomes prior to valinomycin addition and for valinomycin-induced H$^+$ leak observed in protein-free liposomes. FIG. 23 presents the time dependence of the proton uptake per tetramer at pH$_{ex}$=5.5 (time=0 corresponding to the addition of valinomycin). The proton flux is calculated from the initial slope of the curve. The number of conducting protein tetramers is based on the nominal protein content of the sample, halved as a correction for the inability of proteins to activate when oriented with the N-terminal exposed to the high pH$_{in}$. For measurements with amantadine, liposomes are incubated in 100 pM amantadine overnight, and diluted into the external buffer containing 100 pM amantadine.

Example 6

Novel screening of drugs against the proven drug target, the M2 protein of Influenza A, may be achieved using solid state NMR spectroscopy and uniformly aligned samples of the M2 protein. Solid state NMR is a technique that permits the observation of M2 protein in a native-like bilayer environment that assures the native conformation of this viral membrane protein. Changes in the observed frequency of the NMR signals reflect the binding site of the drug to the protein. Uniformly aligned samples of membrane proteins meant that each molecule in the sample will have the same orientation with respect to the magnetic field axis of the NMR spectrometer. In this way the orientation dependent spin interactions such as anisotropic chemical shifts, dipolar and quadrupolar interactions can be observed. The orientations of the individual atomic sites in the protein reflect the orientation of that particular site with respect to the magnetic field. For membrane proteins the plane of the bilayer and hence the orientation of the membrane protein spanning the membrane can be oriented with the bilayer normal either parallel or perpendicular to the magnetic field.

Figure 31:
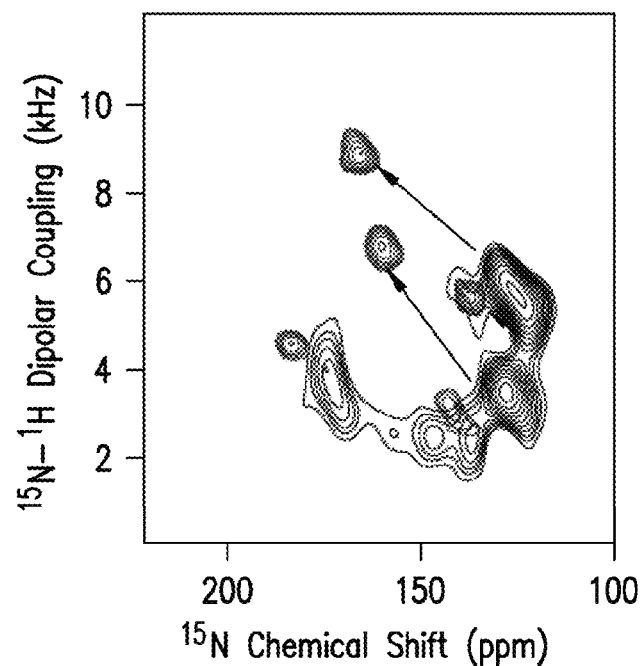
FIG. 31 is a graph an image comparing the solid state NMR spectra of transmembrane domain of M2 protein with (red) and without (blue) the antiviral pore-blocking drug amantadine bound to the protein.

FIG. 31 shows that the binding of amantadine to the transmembrane domain of M2. Ser$^{31}$ of M2 has recently been mutated to glutamine such that amantadine and rimantadine are no longer effective as antiflu drugs for the seasonal flu. Drug screening efforts have continued to focus on the pore binding site for this protein. Embodiments of the invention relate to the unique histidine chemistry that has been identified in this protein (Sharma et al. *Science*, October 22; 330 (6003):509-12 (2010)), see FIG. 32. The histidine tetrad interacts through strong hydrogen bonds distributing two coulombic charges among the four histidine side chains prior to addition of the third charge which initiates H+ transport across the membrane (Sharma et al. *Science*, October 22; 330 (6003):509-12 (2010)). By observing resonances from these sidechains (specific isotope labeling of this amino acid) it will be possible to detect specific binding to the histidine tetrad.

FIGS. 1, 2, 3, 4, 5, 6 and 7 relate to the tetrameric structure of the M2 conductance domain, solved by solid-state NMR spectroscopy and restrained molecular dynamics simulations, in liquid crystalline lipid bilayers. See Examples for details and FIGS. 25-30 for the NMR spectra.

FIG. 1 shows the tetrameric structure of the M2 conductance domain obtained in a lipid bilayer environment and refined by restrained MD in a the same lipid bilayer environment. The TM helix has a substantial tilt with respect to the bilayer normal facilitating drug binding in the pore and the conductance mechanism.

FIG. 2 shows the ribbon representation of the TM and amphipathic helices. One monomer is shown in red. The TM helix is kinked around the highly conserved Gly34 (shown as Ca spheres).

Figure 3:
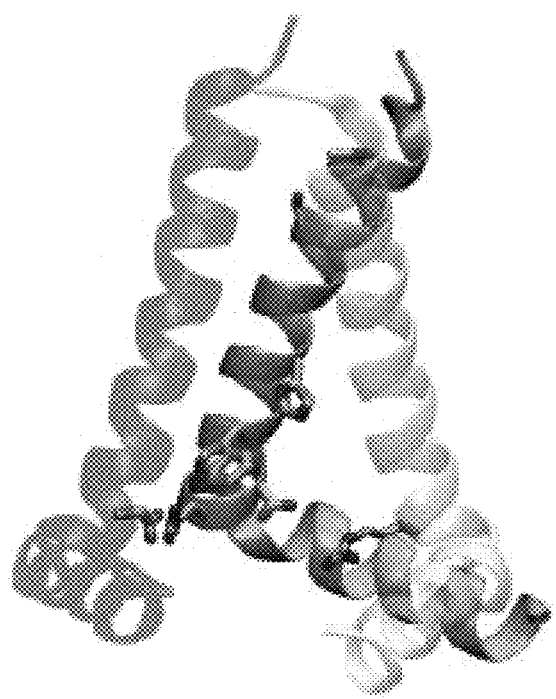
FIG. 3 is a schematic illustration showing that the pore is lined with $Val^{27}$, $Gly^{34}$, $His^{37}$, $Trp^{41}$, $Asp^{44}$, and $Arg^{45}$ residues.

FIG. 3 shows the pore is lined with Val$^{27}$, Gly$^{34}$, His$^{37}$, Trp$^{41}$, Asp$^{44}$, and Arg$^{45}$ residues.

FIG. 4 shows a space-filling representation of the protein side chains in the lipid bilayer environment used for the NMR spectroscopy, structural refinement, and functional assay. C, O, N, and H atoms are colored green, red, blue, and white, respectively. The nonpolar residues of the TM and amphipathic helices form a continuous surface; the positively charged residues of the amphipathic helix are arrayed on the outer edge of the structure in optimal position to interact with charged lipids. The Ser$^{50}$ hydroxyl is also shown to be in an optimal position (as Cys$^{50}$) to accept a palmitoyl group in native membranes.

Figure 5:
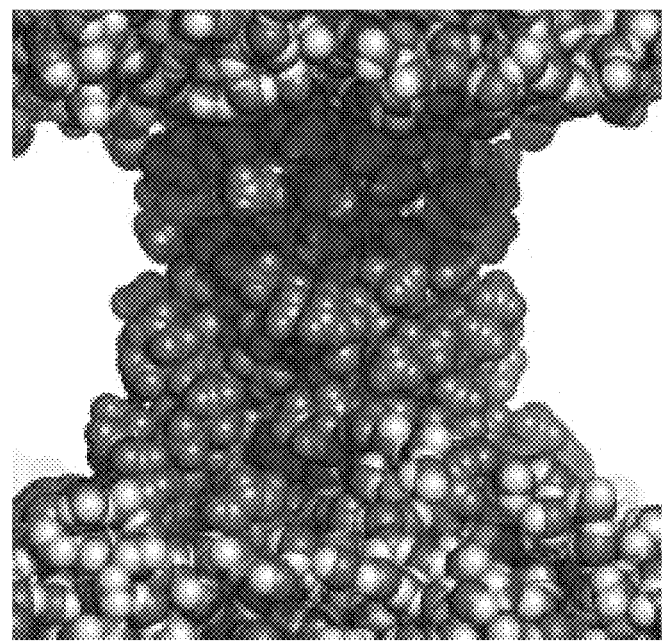
FIG. 5 is a space filling view illustrating that the waters do not have access to the lipid environment.

FIG. 5 shows the space filling view showing that the showing that the waters do not have access to the lipid environment.

FIG. 6 shows a HOLE image (O, S. Smart, J. G. Neduvelil, X. Wang, B. A. Wallace, M. S. Sansom, *J. Mol. Graph.* 14, 354 (1996)) illustrating pore constriction at Val$^{21}$ and Trp$^{41}$.

FIG. 7 shows several key residues at the junction between the TM and amphipathic helices, including Gly$^{58}$ (shown as Cc, spheres), which facilitates the close approach of adjacent monomers, and Ile$^{51}$ and Phe$^{54}$, which fill a pocket previously described as a rimantadine binding site (J. R. Schnell, J. J. Chou, *Nature* 451, 591 (2008)).

Figure 8:
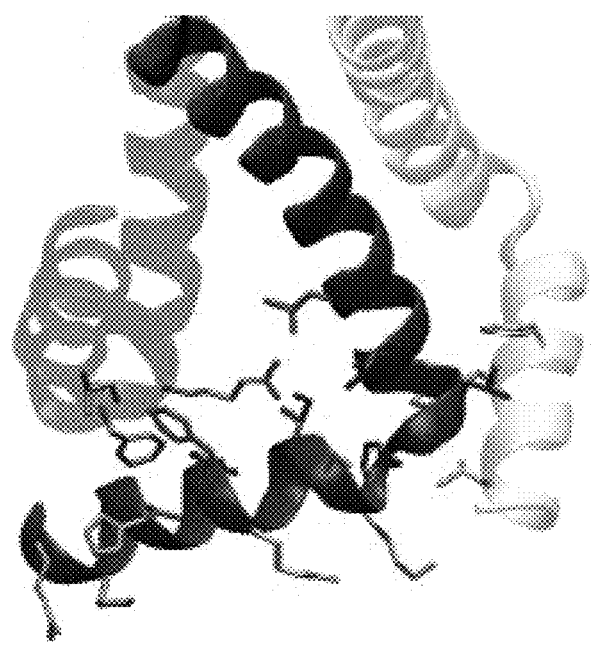
FIG. 8 is a schematic illustration showing that the conductance domain is stabilized by numerous hydrophobic interactions between monomers involving the amphipathic helix bound in the lipid interface.

FIG. 8 shows the conductance domain is stabilized by numerous hydrophobic interactions between monomers involving the amphipathic helix bound in the lipid interface.

Figure 9:
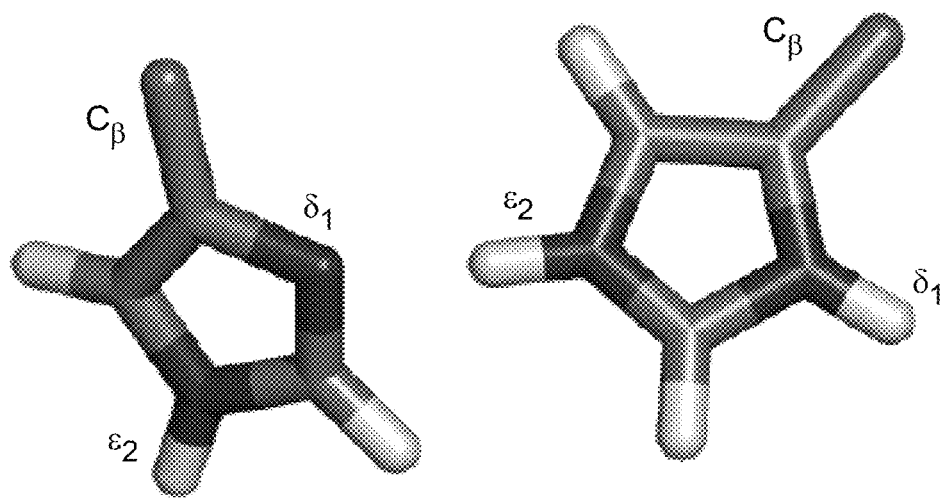
FIG. 9 is a schematic illustration showing the side-view of imidazole-imdazolium dimers having a geometry appropriate for a strong hydrogen bond to form in the restrained MD simulations as predicted from previous NMR studies

FIG. 9 shows a side-view of imidazole-imdazolium dimers having a geometry appropriate for a strong hydrogen bond are shown to form in the restrained MD simulations as predicted from previous NMR studies.

Figure 10:
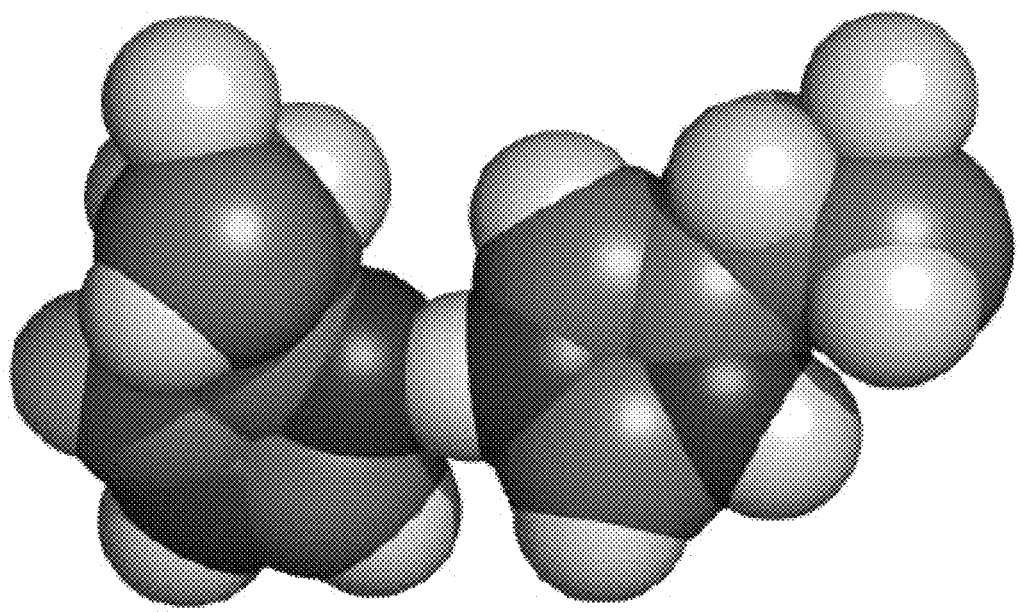
FIG. 10 is a space filling view of FIG. 9 showing that the hydrogen bond is protected from the N-terminal aqueous pore environment.

FIG. 10 shows a space filling view of FIG. 9 showing that the hydrogen bond is protected from the N-terminal aqueous pore environment.

Figure 11:
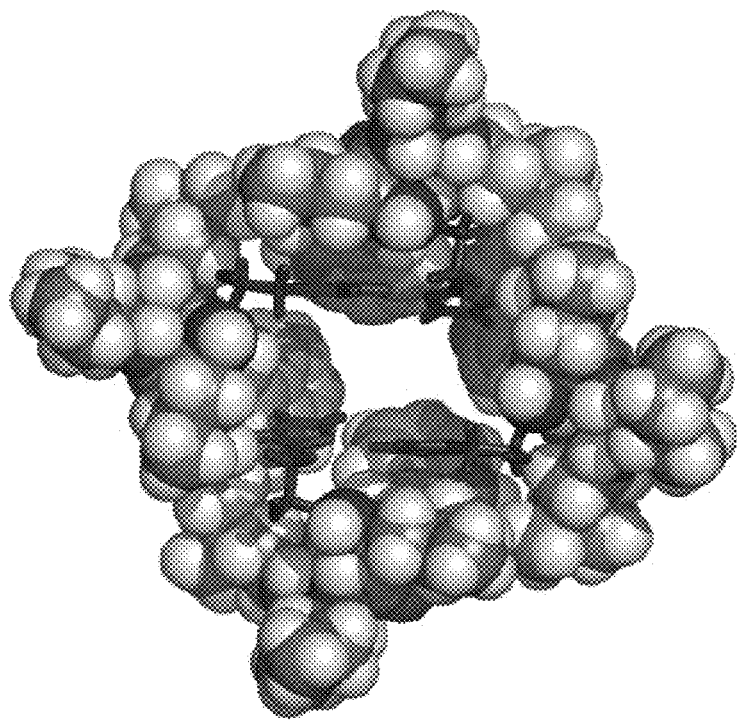
FIG. 11 is a schematic illustration showing the QM-MM calculated histidine tetrad inserted into the refined fourfold symmetric structure.

FIG. 11 shows QM-MM calculated histidine tetrad inserted into the refined fourfold symmetric structure.

FIGS. 12 and 13 relate to the structure of the HxxxW quartet in the histidine-locked state.

FIG. 12 shows the top view of the tetrameric cluster of H$^{37}$XXXw$^{41}$ (His$^{37}$ as sticks and Trp$^{41}$ as spheres). Note the near-coplanar arrangement of each imidazole-imidazolium dimer that forms a strong hydrogen bond between N$_{\delta 1}$ and N$_{\epsilon 2}$. In each dimer, the remaining N$_{\epsilon 2}$ interacts with the indole of a Trp$^{41}$ residue through a cation-$\pi$ interaction. The backbones have four-fold symmetry, as defined by the time-averaged NMR data.

FIG. 13 shows the side view of one of the two imidazole-imidazolium dimers. Both the intraresidue N$_{\delta 1}$—H—O hydrogen bond and the interresidue N$_{\epsilon 2}$—H—N$_{\delta 1}$ strong hydrogen bond can be seen. The near-linearity of the interresidue hydrogen bond is obtained at the expense of a strained C$_\alpha$—C$_\beta$—C$_\gamma$ angle (enlarged by ~10°) of the residue on the left.

Figure 14:
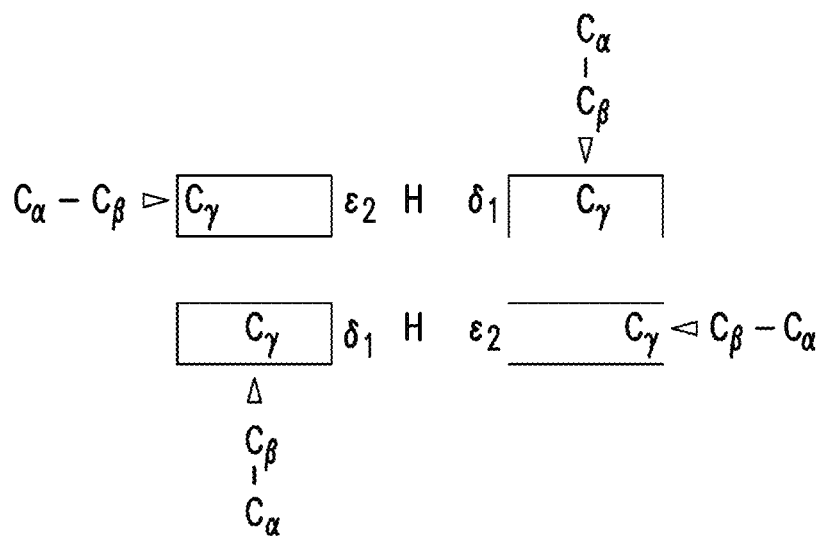
FIG. 14 is a model of the histidine tetrad suggesting a dimer of dimers conformation where the $C_\alpha$ carbons conform to a rectangle.

FIG. 14 shows the histidine tetrad is modeled suggesting a dimer of dimers conformation where the Ca carbons conform to a rectangle.

Figure 15:
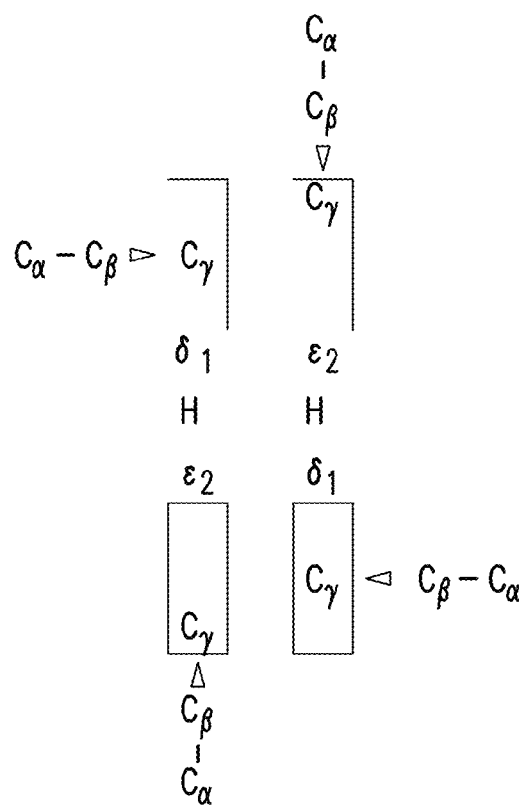
FIG. 15 is a model of the histidine tetrad showing that the rotation of 90° for each of the imidazoles results in breaking and reforming the strong hydrogen bonds.

FIG. 15 shows the rotation of 90° for each of the imidazoles results breaking and reforming the strong hydrogen bonds. The average of these two structures results in the observed four-fold symmetry in the NMR data.

FIGS. 16-19 relate to the conductance mechanism for M2 proton channel involving the conserved HxxxW tetrad.

Figure 16:
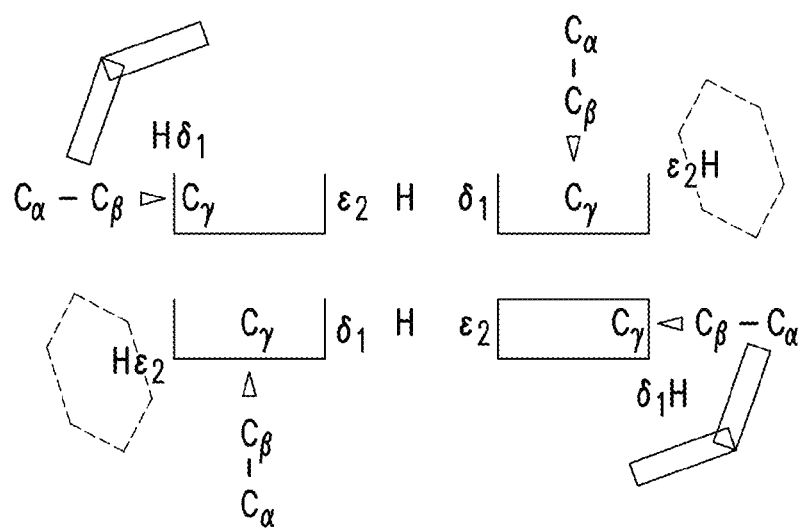
FIG. 16 is an image of the histidine tetrad in a Histidine-Locked +2 Charged State.

FIG. 16 is an image of the histidine tetrad in a Histidine-Locked +2 Charged State. The labeled hydrogens in red are oriented toward the viral interior, while those in black are oriented toward the viral exterior. The imidazole side chains are shown as rectangles, The indole sidechains Involved in cation-$\pi$ interactions are illustrated as hexagons. The His$_{\delta 1}$ protons are shown to be protected by the polypeptide backbone and sidechains of Leu$^{38}$ and Leu$^{40}$ illustrated by a pair of rectangles. The histidine locked state has two pairs of histidine residues, each pair sharing a hydrogen and a Coulombic charge through a strong $\delta 1$-$\epsilon 2$ hydrogen bond.

Figure 17:
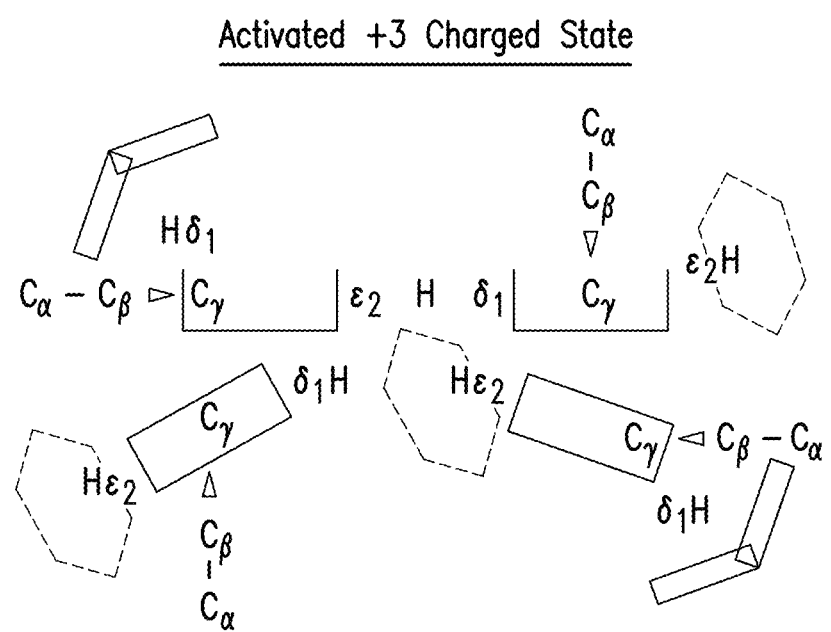
FIG. 17 is an image of the histidine tetrad in an Activated +3 Charged State.

FIG. 17 is an image of the histidine tetrad in an Activated +3 Charged State. The histidine tetrad in the Histidine-Locked +2 charged sate accepts a proton from the N-terminal pore breaking one of the strong hydrogen bonds and generating a +3 charged state. Each imidazolium rotates the nitrogens from the broken hydrogen bond toward the center of the pore and the $\epsilon 2$ protonated site is rotated toward the C-terminal pore where it forms a cation-$\pi$ interaction with an indole.

Figure 18:
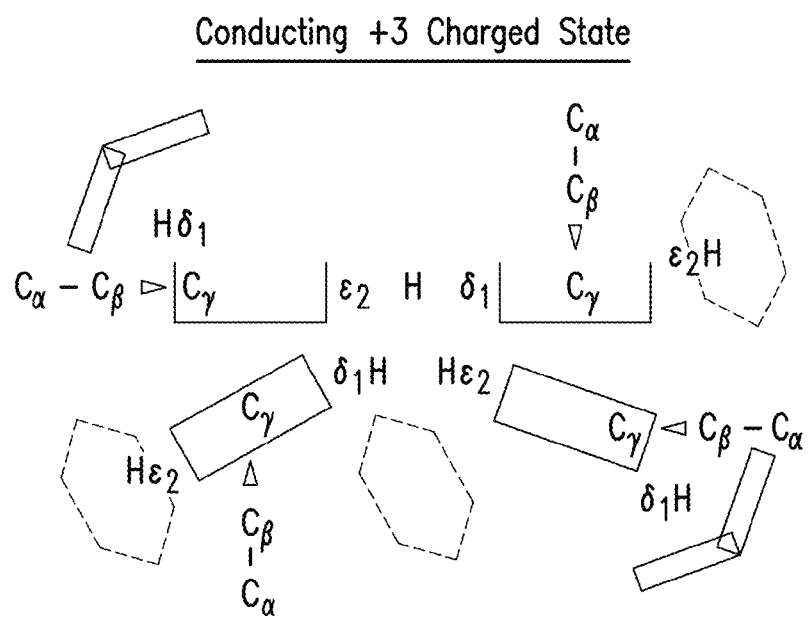
FIG. 18 is an image of the histidine tetrad in a Conducting +3 Charged State.

FIG. 18 is an image of the histidine tetrad in a Conducting +3 Charged State. The conducting state is formed when the indole protecting the newly generated $\epsilon 2$ protonated site is rotated so that water has access to the imidazolium. Once it transfers the proton to water the structure returns to the histidine-locked state as indicated in FIG. 16.

Figure 19:
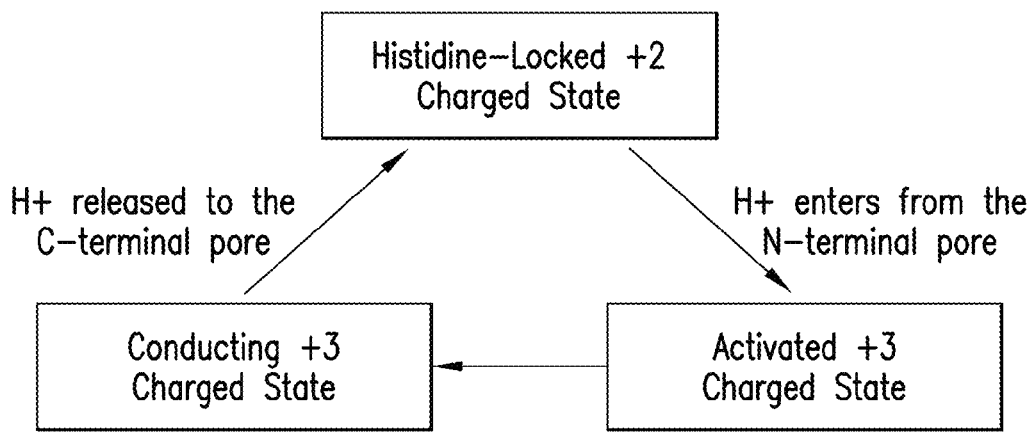
FIG. 19 is an image showing the steps of the Conductance Mechanism for M2 proton channel involving the conserved HxxxW tetrad going through the Histidine-Locked +2 Charged State, Activated +3 Charged State and Conducting +3 Charged State.

FIG. 19 is an image showing the steps of the Conductance Mechanism for M2 proton channel involving the conserved HxxxW tetrad going through the Histidine-Locked +2 Charged State, Activated +3 Charged State and Conducting +3 Charged State.

FIG. 20 Exchange of partners between the two imidazole-imidazolium dimers, leading to apparent C4 symmetry observed by the NMR spectroscopy. The top panel, with AB and CD dimers, is the configuration shown in FIG. 12; the bottom panel models the configuration with AD and BC dimers. The conversion between the two configurations can be accomplished by 90° rotations about $\chi_2$ and 10° changes in C$_\alpha$C$_\beta$C$_\gamma$ angles (so that strained C$_\alpha$C$_\beta$C$_\gamma$ angles become relaxed and vice versa). For such a simple mechanism to work, the $C_\alpha C_\beta$ bonds must be nearly orthogonal to the pore axis, a feature that is indeed observed in the structure determined here. During the configurational conversion, the protons mediating the strong hydrogen bonds between the AB and CD dimers are released to the N-terminal pore, and two other protons from the N-terminal pore are taken up by the AD and BC dimers to form the new strong hydrogen bonds.

FIG. 21 shows a mechanism of acid activation and proton conductance illustrated with half of the HxxxW quartet from a side view. The histidine-locked state (top) is shown with a hydronium ion waiting in the N-terminal pore. Acid activation is initiated with a proton transfer from the hydronium ion into the interresidue hydrogen bond between $N^{\delta 1}$ and Na. In the resulting activated state, the two imidazolium rings rotate so that the two nitrogens move toward the center of the pore; in addition, the protonated $N^{\delta 1}$ forms a hydrogen bond with water in the N-terminal pore while the protonated $N_{\epsilon 2}$ moves downward (via relaxing the $C_\alpha$—$C_\beta$—$C_\gamma$ angle) to form a cation-π interaction with an indole, thereby blocking water access from the C-terminal pore. The conducting state is obtained when this indole moves aside to expose the $N_{\epsilon 2}$ proton to a water in the C-terminal pore. It was suggested previously (M. Yi, T. A. Cross, H, X. Zhou, *Proc. Natl. Acad. Sci. U.S.A.* 106, 13311 (2009)) that the indole motion involves ring rotation coupled to backbone kinking. Once the $N_{\epsilon 2}$ proton is released to C-terminal water, the HxxxW quartet returns to the histidine-locked state.

FIGS. 22 and 23 relate to functional assays of the M2 conductance domain.

FIG. 22 shows the proton uptake per tetramer as a function of time, in the absence (blue) and presence (green) of 100 μM amantadine. $pH_{ex}$=5.5. The initial slopes (lines), after blank subtraction and preliminary drift subtraction, are 140 protons per tetramer per second and 30 protons per tetramer per second, respectively, corresponding to ~80% blockage by amantadine. Proton uptake is extremely selective. Na$^+$ permeability may be ruled out because of a lack of outward proton flux in spite of a strong inward Na$^+$ gradient.

FIG. 23 shows the dependence of proton flux (calculated from the initial slopes illustrated in FIG. 22, without (blue) and with (green) 100 μM amantadine. The error bars each represent 1 S.E., calculated as the square root of the sum of the standard errors of the means for the test group and the control (protein-free liposomes) group. From left to right, the numbers of independent measurements are 6, 5, and 6 without amantadine and 3, 3, and 2 with amantadine. The level of proton conductance observed here at pH 5.5 exceeds those reported previously for similar constructs by an order of magnitude (C. Ma et al., *Proc. Natl. Acad. Sci.* USA 106, 12283 (2009) and R. M. Pielak, J. R. Schnell, J. J. Chou, *Proc. Natl. Acad. Sci.* USA 106, 7379 (2009)). The increased conductance may be attributed to the use of both pH and voltage gradients to drive inward flux, and to the use of acute external acidification to activate the protein.

FIG. 24 shows a SDS PAGE gel of the M2 conductance domain demonstrating the tetrameric state. Molecular weight markers on the left; purified protein in DDM micelles on the right. In comparison, various groups have reported poor tetramer stability of the M2 transmembrane domain in detergent micelles (R. M. Pielak, J. R. Schnell, J. J. Chou, Proc. Natl. Acad. Sci. USA 106, 7379 (2009); G. G. Kochendoerfer et al., *Biochemistry* 38, 11905 (1999) and J. R. Schnell, J. J. Chou, *Nature* 451, 591 (2008)).

FIGS. 25-30 show the $^{15}$N chemical shift and $^{15}$N-$^1$H dipolar coupling correlation (i.e., PISEMA) spectra of the M2 conductance domain in aligned DOPC:DOPE lipid bilayers.

FIG. 25 shows the spectral superposition of $^{15}$N-Ile (blue) and $^{15}$N-Val (black) labeled samples.

FIG. 26 shows the spectral superposition of $^{15}$N-Leu (green) and $^{15}$N-Phe (red) labeled samples.

FIG. 27 shows the spectra of a reverse $^{15}$N labeled sample. Data for TM and amphipathic helices were acquired with different proton offsets.

FIG. 28 shows the PISEMA resonance positions of the protein (original data for Ala$^{29}$, Ala$^{30}$, Gly$^{34}$, and Tyr$^{52}$ not shown). Simulated PISA wheels using ideal helices with tilt angles of 32° and 105° are shown to indicate the TM and amphipathic helices (red and green), respectively. Dipolar couplings are shown as sign-sensitive.

Figure 29:
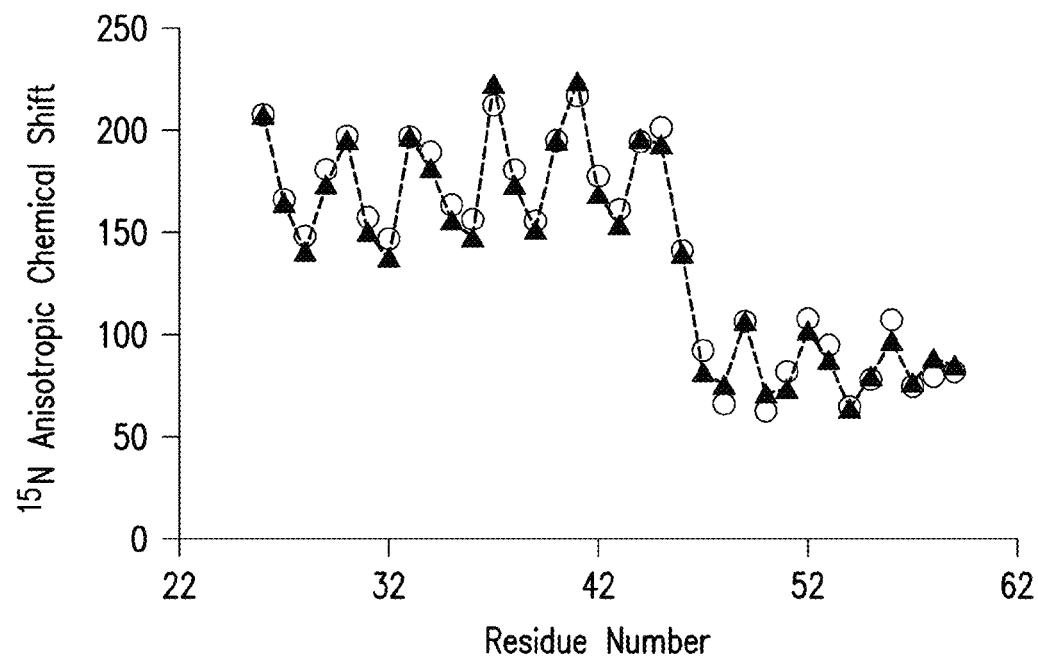
FIG. 29 is a graph showing the comparison of experimental dipolar couplings (blue triangles connected by dashed lines) and those calculated on the refined structure (red circles)

FIG. 29 shows the comparison of experimental dipolar couplings (blue triangles connected by dashed lines) and those calculated on the refined structure (red circles).

Figure 30:
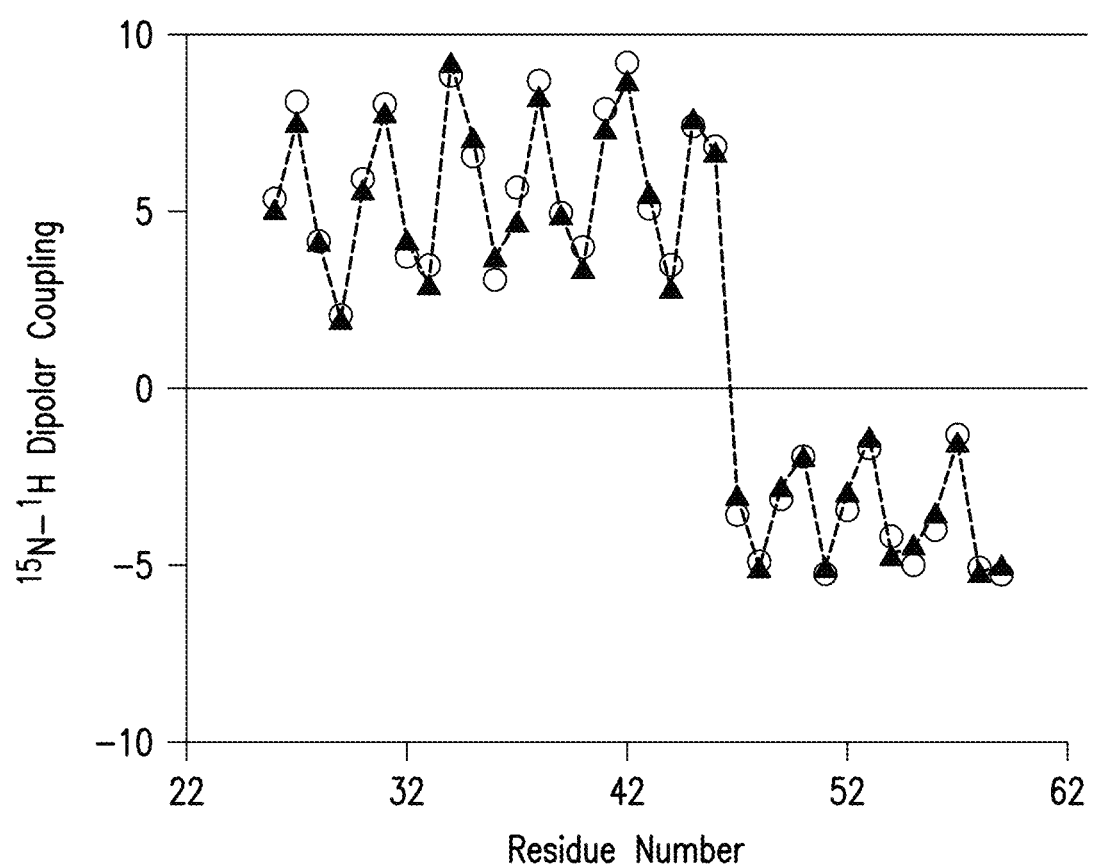
FIG. 30 is a graph showing the similar comparison as FIG. 29 for chemical shifts.

FIG. 30 shows a similar comparison for chemical shifts. Experimental data for Lys$^{60}$ and Arg$^{61}$ were not used for structural calculation due to their considerable dynamics (as indicated by near isotropic chemical shifts and small dipolar couplings).

FIG. 31 shows an image comparing the solid state NMR spectra of transmembrane domain of M2 protein with (red) and without (blue) the antiviral pore-blocking drug amantadine bound to the protein. Five isoleucine amino acids are $^{15}$N labeled in this sample and two of the resonances shift (arrows) dramatically in response to drug binding identifying the structural change induced by drug binding.

Figure 32:
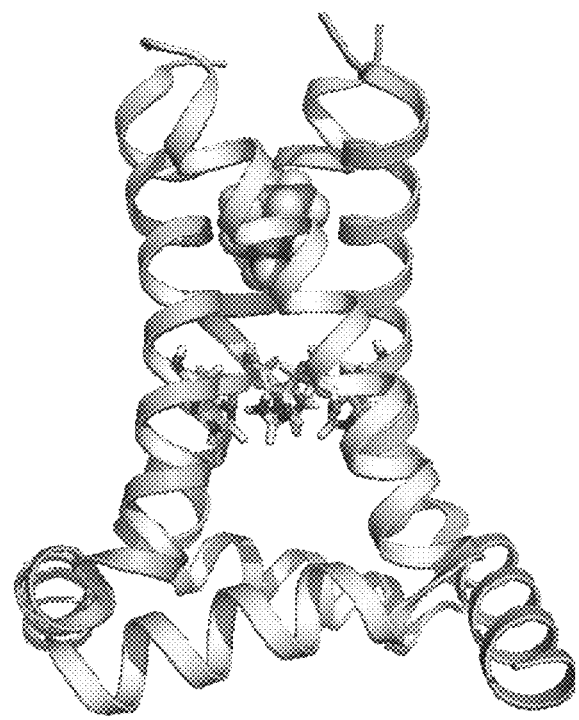
FIG. 32 is a schematic illustration showing the structure of the conductance domain (including the transmembrane domain) determined by solid state NMR (Sharma et al., *Science* 330, 509 (2010)).

FIG. 32 shows the structure of the conductance domain (including the transmembrane domain) determined by solid state NMR (Sharma et al., *Science* 330, 509 (2010)). The antiflu drug is show in its pore binding site (Cady et al., *Nature*, 2010). The unique histidine chemistry from HxxxW quartet is shown to be well separated from the amantadine binding site.

In the claims, unless specified otherwise, steps of a method may be performed in any order. For example, in a method claim, step (b) may be performed before step (a), unless the language of the claim requires that step (a) be performed prior to step (b).

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising the following steps:
    (a) providing a first solid-state NMR spectrum and a second solid-state NMR spectrum, and
    (b) detecting a change in resonance of a labeled isotope based on comparing the second solid-state NMR spectrum to the first solid-state NMR spectrum to thereby determine that a drug candidate has bound to a histidine tetrad of a viral protein,
    wherein first solid-state NMR spectrum is for a first uniformly aligned sample of the viral protein, and
    wherein the second solid-state spectrum is for a second uniformly aligned sample of the viral protein after being treated with the drug candidate.

2. The method according to claim 1, wherein the second uniformly aligned sample is the first uniformly aligned sample after the viral protein in the first uniformly aligned sample has being treated with the drug candidate.

3. The method of claim 2, comprising the following steps:
(c) forming the second uniformly aligned sample of the viral protein by treating the viral protein of the first uniformly aligned sample with the drug candidate.

4. The method according to claim 1, wherein the viral protein is a channel protein.

5. The method according to claim 4, wherein the channel protein is an M2 protein of Influenza A virus.

6. The method of claim 1, wherein the method comprises the following step:
(c) generating the first solid-state NMR spectrum.

7. The method of claim 1, wherein the method comprises the following step:
(c) generating the second solid-state NMR spectrum.

8. The method of claim 1, comprising the following steps:
(c) forming the second uniformly aligned sample of the viral protein by treating the viral protein of a third uniformly aligned sample with the drug candidate.

\* \* \* \* \*